United States Patent
Earles et al.

(12)

(10) Patent No.: US 11,779,751 B2
(45) Date of Patent: **\*Oct. 10, 2023**

(54) BLOOD PUMPS

(71) Applicant: PROCYRION, INC., Houston, TX (US)

(72) Inventors: Ronald G. Earles, Houston, TX (US); Jason J. Heuring, Houston, TX (US); Christopher A. Durst, Houston, TX (US); Omar M. Benavides, Houston, TX (US)

(73) Assignee: PROCYRION, INC., Houston, TX (US)

(\*) Notice: Subject to any disclaimer, the term of this patent is extended or adjusted under 35 U.S.C. 154(b) by 0 days.

This patent is subject to a terminal disclaimer.

(21) Appl. No.: 17/935,036

(22) Filed: Sep. 23, 2022

(65) Prior Publication Data
US 2023/0020104 A1 Jan. 19, 2023

Related U.S. Application Data

(63) Continuation of application No. 17/535,303, filed on Nov. 24, 2021, now Pat. No. 11,452,859, which is a
(Continued)

(51) Int. Cl.
*A61M 60/139* (2021.01)
*A61M 60/419* (2021.01)
(Continued)

(52) U.S. Cl.
CPC .......... *A61M 60/139* (2021.01); *A61M 60/13* (2021.01); *A61M 60/221* (2021.01);
(Continued)

(58) Field of Classification Search
CPC .............. A61M 60/139; A61M 60/585; A61M 60/226; A61M 60/419; A61M 60/221;
(Continued)

(56) References Cited

U.S. PATENT DOCUMENTS 2,896,926 A 7/1959 Chapman
2,935,068 A 5/1960 Donaldson
(Continued)

FOREIGN PATENT DOCUMENTS

EP 2388029 11/2011
WO WO 1998/000185 1/1988
(Continued)

OTHER PUBLICATIONS

Demirsoy, Ergun et al., Grafting the restenosed coronary artery after removal of multiple failed stents by endarterectomy, Texas Heart Institute Journal, Endarterectomy of Multiple Stents Before Grafts, 2006, vol. 33, No. 2, pp. 262-263.
(Continued)

*Primary Examiner* — Erin M Piateski
(74) *Attorney, Agent, or Firm* — Knobbe, Martens, Olson & Bear LLP

(57) ABSTRACT

A blood flow assist system can include an impeller assembly including an impeller shaft and an impeller on the impeller shaft, a primary flow pathway disposed along an exterior surface of the impeller. The system can include a rotor assembly at a proximal portion of the impeller shaft. A secondary flow pathway can be disposed along a lumen of the impeller shaft. During operation of the blood flow assist system, blood can be pumped proximally along the primary flow pathway and the secondary flow pathway. The system can include a sleeve bearing distal the impeller. The system can include a drive unit having a distal end disposed distal a proximal end of the second impeller. The drive unit comprising a drive magnet and a drive bearing between the drive magnet and the impeller assembly.

30 Claims, 16 Drawing Sheets

Related U.S. Application Data continuation of application No. PCT/US2020/062928, filed on Dec. 2, 2020.

(60) Provisional application No. 62/947,940, filed on Dec. 13, 2019, provisional application No. 62/943,062, filed on Dec. 3, 2019.

(51) Int. Cl.

| | |
|---|---|
| *A61M 60/221* | (2021.01) |
| *A61M 60/824* | (2021.01) |
| *A61M 60/585* | (2021.01) |
| *A61M 60/226* | (2021.01) |
| *A61M 60/13* | (2021.01) |
| *A61M 60/825* | (2021.01) |
| *F04D 13/02* | (2006.01) |
| *F04D 29/046* | (2006.01) |
| *F04D 7/00* | (2006.01) |
| *F04D 13/06* | (2006.01) |
| *F04D 29/043* | (2006.01) |
| *F04D 29/52* | (2006.01) |
| *F04D 29/18* | (2006.01) |
| *A61M 60/808* | (2021.01) |
| *A61M 60/82* | (2021.01) |

(52) U.S. Cl.
CPC ........ *A61M 60/226* (2021.01); *A61M 60/419* (2021.01); *A61M 60/585* (2021.01); *A61M 60/824* (2021.01); *A61M 60/825* (2021.01); *F04D 7/00* (2013.01); *F04D 13/026* (2013.01); *F04D 13/06* (2013.01); *F04D 29/043* (2013.01); *F04D 29/0467* (2013.01); *F04D 29/181* (2013.01); *F04D 29/528* (2013.01); *A61M 60/808* (2021.01); *A61M 60/82* (2021.01)

(58) Field of Classification Search
CPC .. A61M 60/824; A61M 60/13; A61M 60/825; A61M 60/808; A61M 60/82; F04D 7/00; F04D 13/026; F04D 13/06; F04D 29/043; F04D 29/0467; F04D 29/181; F04D 29/528
USPC .......................................................... 600/16
See application file for complete search history.

(56) References Cited

U.S. PATENT DOCUMENTS

| | | |
|---|---|---|
| 3,455,540 A | 7/1969 | Marcmann |
| 3,510,229 A | 7/1970 | Smith |
| 3,620,584 A | 11/1971 | Rosenweig |
| 3,812,812 A | 5/1974 | Hurwitz |
| 4,127,384 A | 11/1978 | Fahlvik et al. |
| 4,141,603 A | 2/1979 | Remmers et al. |
| 4,304,524 A | 12/1981 | Coxon |
| 4,407,508 A | 10/1983 | Raj et al. |
| 4,613,329 A | 9/1986 | Bodicky |
| 4,625,712 A | 12/1986 | Wampler |
| 4,643,641 A | 2/1987 | Clausen et al. |
| 4,753,221 A | 6/1988 | Kensey et al. |
| 4,846,152 A | 7/1989 | Wampler et al. |
| 4,900,227 A | 2/1990 | Trouplin |
| 4,919,647 A | 4/1990 | Nash |
| 4,944,722 A | 7/1990 | Carriker et al. |
| 4,969,865 A | 11/1990 | Hwang et al. |
| 4,994,017 A | 2/1991 | Yozu |
| 5,007,513 A | 4/1991 | Carlson |
| 5,147,388 A | 9/1992 | Yamazaki |
| 5,201,679 A | 4/1993 | Velte, Jr. et al. |
| 5,207,695 A | 5/1993 | Trout, III |
| 5,211,546 A | 5/1993 | Isaacson et al. |
| 5,368,438 A | 11/1994 | Raible |
| 5,393,197 A | 2/1995 | Lemont et al. |
| 5,405,383 A | 4/1995 | Barr |
| 5,490,763 A | 2/1996 | Abrams et al. |
| 5,527,159 A | 6/1996 | Bozeman, Jr. et al. |
| 5,534,287 A | 7/1996 | Lukic |
| 5,588,812 A | 12/1996 | Taylor et al. |
| 5,613,935 A | 3/1997 | Jarvik |
| 5,660,397 A | 8/1997 | Holtkamp |
| 5,686,045 A | 11/1997 | Carter |
| 5,722,930 A | 3/1998 | Larson, Jr. et al. |
| 5,725,570 A | 3/1998 | Heath |
| 5,749,855 A | 5/1998 | Reitan |
| 5,824,070 A | 10/1998 | Jarvik |
| 5,827,171 A | 10/1998 | Dobak, III et al. |
| 5,911,685 A | 6/1999 | Siess et al. |
| 5,921,913 A | 7/1999 | Seiss |
| 5,947,703 A | 9/1999 | Nojiri et al. |
| 5,951,263 A | 9/1999 | Taylor et al. |
| 5,964,694 A | 10/1999 | Siess et al. |
| 6,007,478 A | 12/1999 | Siess et al. |
| 6,136,025 A | 10/2000 | Barbut et al. |
| 6,227,797 B1 | 5/2001 | Watterson et al. |
| 6,245,026 B1 | 6/2001 | Campbell et al. |
| 6,253,769 B1 | 7/2001 | LaFontaine et al. |
| 6,302,910 B1 | 10/2001 | Yamazaki et al. |
| 6,517,315 B2 | 2/2003 | Belady |
| 6,527,699 B1 | 3/2003 | Goldowsky |
| 6,533,716 B1 | 3/2003 | Schmitz-Rode et al. |
| 6,547,519 B2 | 4/2003 | deBlanc et al. |
| 6,585,756 B1 | 7/2003 | Strecker |
| 6,609,883 B2 | 8/2003 | Woodard et al. |
| 6,616,323 B2 | 9/2003 | McGill |
| 6,638,011 B2 | 10/2003 | Woodard et al. |
| 6,645,241 B1 | 11/2003 | Strecker |
| 6,660,014 B2 | 12/2003 | Demarais et al. |
| 6,716,189 B1 | 4/2004 | Jarvik et al. |
| 6,733,459 B1 | 5/2004 | Atsumi |
| 6,749,598 B1 | 6/2004 | Keren et al. |
| 6,860,713 B2 | 3/2005 | Hoover |
| 6,866,805 B2 | 3/2005 | Hong et al. |
| 6,887,215 B2 | 5/2005 | McWeeney |
| 6,972,956 B2 | 12/2005 | Franz et al. |
| 7,011,620 B1 | 3/2006 | Seiss |
| 7,125,376 B2 | 10/2006 | Viole et al. |
| 7,189,260 B2 | 3/2007 | Harvath et al. |
| 7,374,531 B1 | 5/2008 | Kantrowitz |
| 7,381,034 B2 | 6/2008 | Shishido |
| 7,393,181 B2 | 7/2008 | McBride et al. |
| 7,396,327 B2 | 7/2008 | Morello |
| 7,473,220 B2 | 1/2009 | Francese et al. |
| 7,534,258 B2 | 5/2009 | Gomez et al. |
| 7,682,673 B2 | 3/2010 | Houston et al. |
| 7,758,806 B2 | 7/2010 | Zhao |
| 7,762,941 B2 | 7/2010 | Jarik |
| 7,841,976 B2 | 11/2010 | McBride et al. |
| 7,878,967 B1 | 2/2011 | Khanal |
| 7,914,436 B1 | 3/2011 | Kung |
| 7,993,259 B2 | 8/2011 | Kang et al. |
| 7,998,054 B2 | 8/2011 | Bolling |
| 8,012,079 B2 | 9/2011 | Delgado, III |
| 8,088,059 B2 | 1/2012 | Jarvik |
| 8,123,669 B2 | 2/2012 | Siess et al. |
| 8,177,703 B2 | 5/2012 | Smith et al. |
| 8,403,824 B2 | 3/2013 | Foster |
| 8,579,858 B2 | 11/2013 | Reitan et al. |
| 8,591,393 B2 | 11/2013 | Walters et al. |
| 8,597,170 B2 | 12/2013 | Walters et al. |
| 8,641,594 B2 | 2/2014 | LaRose et al. |
| 8,727,959 B2 | 5/2014 | Reitan et al. |
| 8,731,664 B2 | 5/2014 | Foster et al. |
| 8,734,508 B2 | 5/2014 | Hastings et al. |
| 8,777,832 B1 | 7/2014 | Wang et al. |
| 8,992,407 B2 | 3/2015 | Smith et al. |
| 9,138,517 B2 | 9/2015 | Garrigue |
| 9,138,518 B2 | 9/2015 | Campbell et al. |
| 9,144,638 B2 | 9/2015 | Zimmermann et al. |
| 9,162,018 B2 | 10/2015 | Foster |
| 9,199,020 B2 | 12/2015 | Siess |

(56) References Cited

U.S. PATENT DOCUMENTS

| | | |
|---|---|---|
| 9,265,870 B2 | 2/2016 | Reichenbach et al. |
| 9,364,593 B2 | 6/2016 | McBride et al. |
| 9,415,147 B2 | 8/2016 | Akkerman et al. |
| 9,433,713 B2 | 9/2016 | Corbett et al. |
| 9,486,566 B2 | 11/2016 | Siess |
| 9,533,084 B2 | 1/2017 | Siess et al. |
| 9,572,915 B2 | 2/2017 | Heuring et al. |
| 9,616,159 B2 | 4/2017 | Anderson et al. |
| 9,744,281 B2 | 8/2017 | Siegenthaler |
| 9,759,222 B2 | 9/2017 | Zimmermann et al. |
| 9,777,732 B2 | 10/2017 | LaRose et al. |
| 9,907,890 B2 | 3/2018 | Muller |
| 9,919,089 B2 | 3/2018 | Garrigue |
| 10,039,873 B2 | 8/2018 | Siegenthaler |
| 10,111,994 B2 | 10/2018 | Wu et al. |
| 10,195,324 B2 | 2/2019 | Foster |
| 10,201,645 B2 | 2/2019 | Muller |
| 10,413,648 B2 | 9/2019 | Delgado, III |
| 10,443,738 B2 | 10/2019 | Durst et al. |
| 10,722,627 B1 | 7/2020 | Obeid et al. |
| 11,235,138 B2 | 2/2022 | Gross-Hardt et al. |
| 11,241,569 B2 | 2/2022 | Delgado |
| 11,325,138 B2 | 2/2022 | Gross-Hardt et al. |
| 11,324,940 B2 | 5/2022 | Earles et al. |
| 11,351,359 B2 | 6/2022 | Clifton et al. |
| 11,452,859 B2 | 9/2022 | Earles et al. |
| 11,471,665 B2 | 10/2022 | Clifton et al. |
| 11,517,736 B2 | 12/2022 | Earles et al. |
| 11,571,559 B2 | 2/2023 | Clifton et al. |
| 11,642,511 B2 | 5/2023 | Delgado |
| 2002/0018713 A1 | 2/2002 | Woodard et al. |
| 2002/0151761 A1 | 10/2002 | Viole et al. |
| 2002/0169413 A1 | 11/2002 | Keren et al. |
| 2003/0105383 A1 | 6/2003 | Barbut et al. |
| 2003/0144574 A1 | 7/2003 | Heilman et al. |
| 2003/0176912 A1 | 9/2003 | Chuter et al. |
| 2003/0233143 A1 | 12/2003 | Gharib et al. |
| 2004/0044266 A1 | 3/2004 | Siess et al. |
| 2004/0046466 A1 | 3/2004 | Siess et al. |
| 2004/0215050 A1* | 10/2004 | Morello ............ A61M 60/538 600/17 |
| 2005/0131271 A1 | 6/2005 | Benkowski et al. |
| 2005/0220636 A1 | 10/2005 | Henein et al. |
| 2006/0036127 A1 | 2/2006 | Delgado, III |
| 2006/0062672 A1 | 3/2006 | McBride et al. |
| 2006/0155159 A1 | 7/2006 | Melvin |
| 2007/0004959 A1 | 1/2007 | Carrier et al. |
| 2007/0156006 A1 | 7/2007 | Smith et al. |
| 2008/0103591 A1 | 5/2008 | Siess |
| 2009/0093764 A1 | 4/2009 | Pfeffer et al. |
| 2009/0149950 A1 | 6/2009 | Wampler |
| 2010/0174131 A1 | 7/2010 | Foster et al. |
| 2010/0249489 A1 | 9/2010 | Jarvik |
| 2011/0106115 A1 | 5/2011 | Haselby et al. |
| 2011/0152999 A1 | 6/2011 | Hastings et al. |
| 2011/0160844 A1 | 6/2011 | Haselby et al. |
| 2011/0238172 A1 | 9/2011 | Akdis |
| 2011/0318204 A1 | 12/2011 | Omori |
| 2012/0029265 A1 | 2/2012 | LaRose et al. |
| 2012/0134832 A1 | 5/2012 | Wu |
| 2012/0172654 A1 | 7/2012 | Bates |
| 2013/0053623 A1 | 2/2013 | Evans et al. |
| 2013/0303831 A1 | 11/2013 | Evans |
| 2014/0128659 A1 | 5/2014 | Heuring et al. |
| 2014/0200664 A1 | 7/2014 | Akkerman et al. |
| 2014/0275722 A1* | 9/2014 | Zimmermann ..... A61M 60/148 600/16 |
| 2014/0275726 A1 | 9/2014 | Zeng |
| 2015/0258260 A1 | 9/2015 | Tuseth |
| 2015/0285258 A1 | 10/2015 | Foster |
| 2015/0364863 A1 | 12/2015 | Andrus et al. |
| 2016/0045652 A1 | 2/2016 | Cornen |
| 2016/0045653 A1 | 2/2016 | Siess |
| 2016/0303299 A1 | 10/2016 | Muller |
| 2016/0346450 A1 | 12/2016 | Akkerman et al. |
| 2017/0014562 A1 | 1/2017 | Liebing |
| 2017/0043074 A1 | 2/2017 | Siess |
| 2017/0087288 A1 | 3/2017 | Grob-Hardt et al. |
| 2017/0188903 A1 | 7/2017 | Bernstein |
| 2017/0197019 A1 | 7/2017 | Tuseth et al. |
| 2017/0216507 A1 | 8/2017 | Kushwaha et al. |
| 2017/0296720 A1 | 10/2017 | Taskin et al. |
| 2017/0340789 A1 | 11/2017 | Bonde et al. |
| 2018/0010608 A1 | 1/2018 | LaRose et al. |
| 2018/0050139 A1 | 2/2018 | Siess et al. |
| 2018/0050140 A1 | 2/2018 | Siess et al. |
| 2018/0050142 A1 | 2/2018 | Dur et al. |
| 2018/0064861 A1 | 3/2018 | Garrigue |
| 2018/0154057 A1 | 6/2018 | Barry |
| 2018/0169312 A1 | 6/2018 | Sun |
| 2018/0193543 A1* | 7/2018 | Sun ..................... A61M 60/30 |
| 2018/0228953 A1* | 8/2018 | Siess .................. A61M 60/825 |
| 2018/0236150 A1 | 8/2018 | Arnold et al. |
| 2018/0296743 A1 | 10/2018 | Siegenthaler |
| 2018/0303991 A1 | 10/2018 | Nusser et al. |
| 2018/0311421 A1 | 11/2018 | Tuseth et al. |
| 2019/0001034 A1 | 1/2019 | Taskin et al. |
| 2019/0060543 A1 | 2/2019 | Khanal et al. |
| 2019/0097353 A1 | 3/2019 | McSweeney |
| 2019/0125948 A1 | 5/2019 | Stanfield et al. |
| 2019/0143018 A1 | 5/2019 | Salahieh et al. |
| 2019/0269840 A1 | 9/2019 | Tuval et al. |
| 2019/0275224 A1 | 9/2019 | Hanson et al. |
| 2019/0290816 A1 | 9/2019 | Petersen |
| 2019/0298902 A1 | 10/2019 | Siess et al. |
| 2019/0328948 A1* | 10/2019 | Salahieh ............. A61M 60/174 |
| 2019/0358382 A1 | 11/2019 | Delgado, III |
| 2020/0076271 A1 | 3/2020 | Sconzert et al. |
| 2020/0121835 A1 | 4/2020 | Farago et al. |
| 2020/0306434 A1 | 10/2020 | VanCamp et al. |
| 2020/0316277 A1 | 10/2020 | Delgado, III |
| 2020/0316278 A1 | 10/2020 | Delgado |
| 2021/0008264 A1 | 1/2021 | Radman |
| 2021/0046231 A1 | 2/2021 | Weber et al. |
| 2021/0052793 A1 | 2/2021 | Struthers et al. |
| 2021/0060223 A1 | 3/2021 | Weber et al. |
| 2021/0060224 A1 | 3/2021 | Kronstedt et al. |
| 2021/0069393 A1 | 3/2021 | Schauer et al. |
| 2021/0069397 A1 | 3/2021 | Chouinard et al. |
| 2021/0100940 A1 | 4/2021 | Breidall et al. |
| 2021/0162196 A1 | 6/2021 | Georges et al. |
| 2021/0220634 A1 | 7/2021 | Cook |
| 2021/0220636 A1 | 7/2021 | Schauer et al. |
| 2021/0220637 A1 | 7/2021 | Edwards et al. |
| 2021/0260360 A1 | 8/2021 | Georges et al. |
| 2021/0275796 A1 | 9/2021 | Struthers et al. |
| 2021/0346680 A1 | 11/2021 | Vogt et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0226634 A1 | 7/2022 | Gross-Hardt et al. |
| 2022/0257920 A1 | 8/2022 | Earles et al. |
| 2022/0296880 A1 | 9/2022 | Clifton et al. |
| 2023/0060591 A1 | 3/2023 | Clifton et al. |
| 2023/0020104 A1 | 4/2023 | Earles et al. |

FOREIGN PATENT DOCUMENTS

| | | |
|---|---|---|
| WO | WO 00/33446 | 6/2000 |
| WO | WO 01/10342 A1 | 2/2001 |
| WO | WO 02/070039 A2 | 9/2002 |
| WO | WO 03/103745 A2 | 12/2003 |
| WO | WO 2005/016416 A1 | 2/2005 |
| WO | WO 2005/020848 A2 | 3/2005 |
| WO | WO 2009/046779 | 4/2009 |
| WO | WO 2009/091968 | 7/2009 |
| WO | WO 2017/165372 | 9/2017 |
| WO | WO 2018/096531 | 5/2018 |
| WO | WO 2019/094963 | 5/2019 |
| WO | WO 2019/173596 | 9/2019 |
| WO | WO 2021/062565 | 4/2021 |
| WO | WO 2021/062566 | 4/2021 |
| WO | WO 2021/113389 | 6/2021 |

(56) References Cited

FOREIGN PATENT DOCUMENTS

| WO | WO 2021/117021 | 6/2021 |
|---|---|---|
| WO | WO 2021/119413 | 6/2021 |
| WO | WO 2021/138673 | 7/2021 |
| WO | WO 2022/256333 | 12/2022 |

OTHER PUBLICATIONS

Greenberg, B., Rationale, Design and Methods for a Pivotal Randomized Clinical Trial of Continuous Aortic Flow Augmentation in Patients with Exacrbation of Heart Failure: The Momentum Trial, Journal of Cardiac Failure, 2007, vol. 13, No. 9, pp. 715-721.

Herzum, M. et al., Managing a complication after direct stenting; removal of a maldeployed stent with rotational artherectomy, Heart Jrnl 2005: 91: e46, URL: http://www.heartjnl.com/cgi/content/full/91/6/e46).

Siess, T. et al., "From a lab type to a product: A retrospective view on Impella's assist technology," Artificial Organs, Jan. 15, 2002, vol. 25, Issue 5, pp. 414-421.

Triantafyllou, K.D. et al., Coronary endarterectomy and stent removal with of-pump coronary artery bypass surgery, Heart Journal, Images in Cardiology, dai: 10.1136/hrt.2005.076687, p. 885.

Vazquez, R. et al., Plasma protein denaturation with graded heat exposure, Perfusion, 2013, vol. 28, No. 6, pp. 557-559.

European Search Report, EP09175307.9, dated Dec. 18, 2009.

International Search report of PCT/US2005/028875, dated Dec. 16, 2005.

Written Opinion of the International Searching Authority, PCT/US2005/028875, dated Dec. 15, 2005.

International Search Report and Written Opinion for PCT/US2013/033894, dated Jun. 17, 2013.

International Search Report and Written Opinion issued in PCT Application No. PCT/US2020/064489, dated Apr. 8, 2021, in 26 pages.

International Search Report and Written Opinion issued in PCT Application No. PCT/US2020/062928, dated Apr. 9, 2021, in 26 pages.

Notice of Allowance dated Oct. 1, 2021, in U.S. Appl. No. 15/276,590, 14 pages.

\* cited by examiner

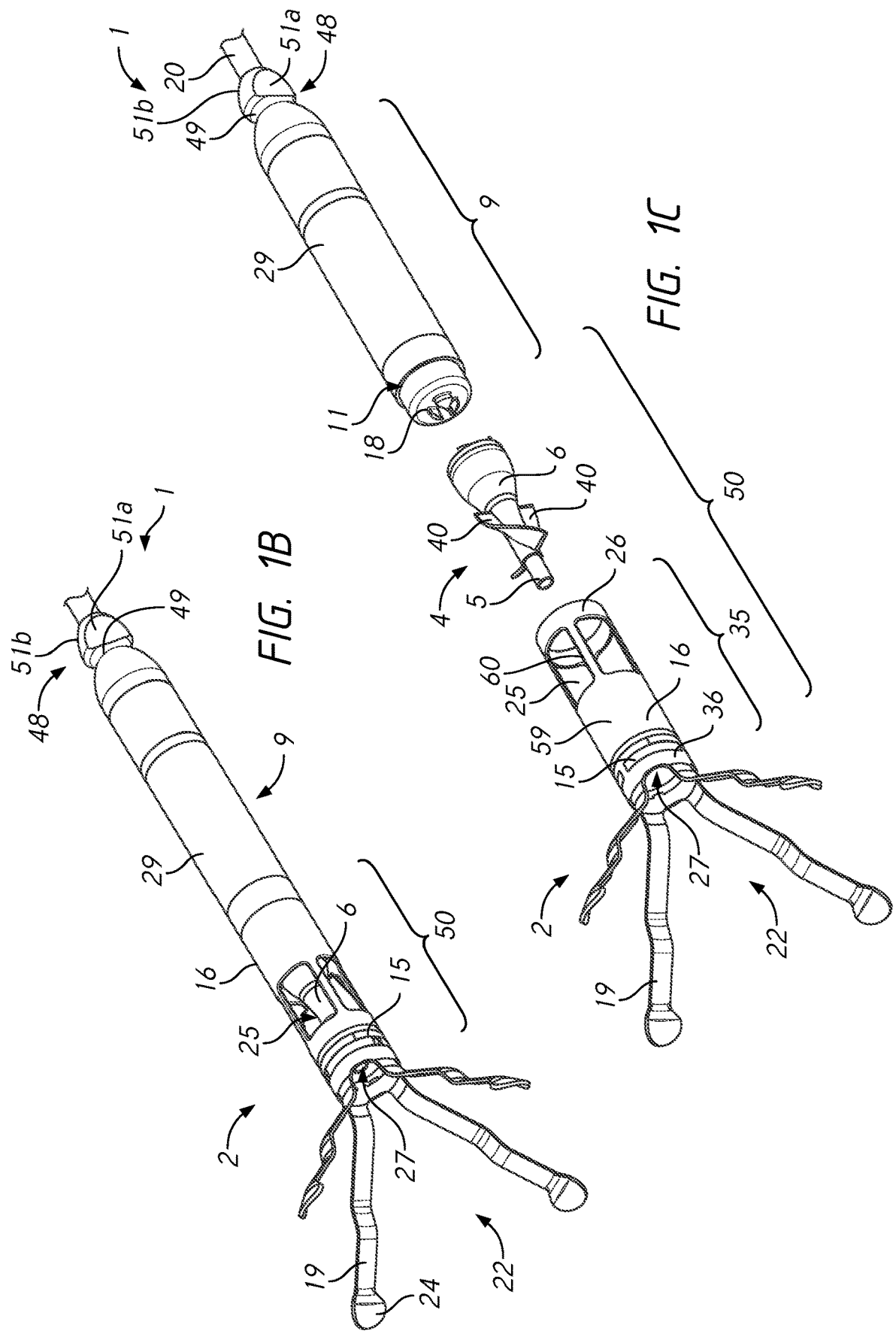

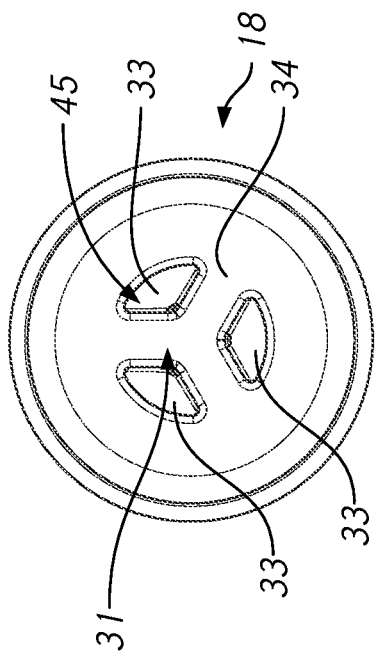
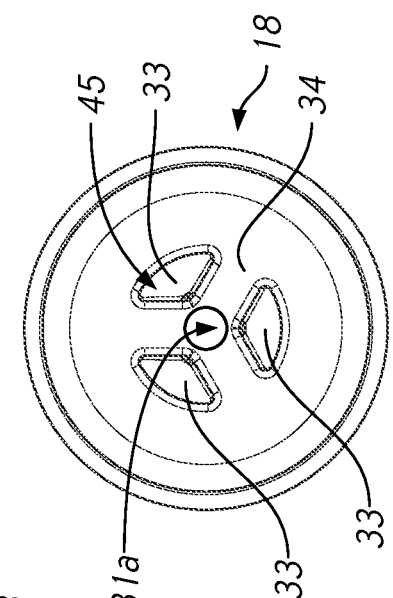
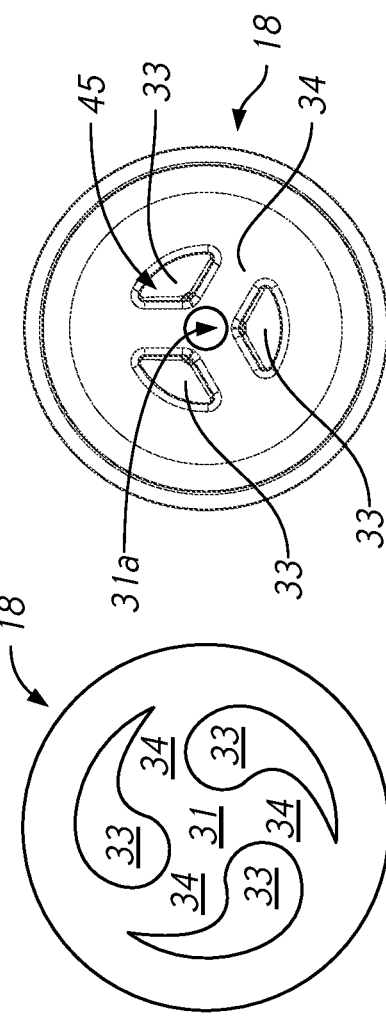
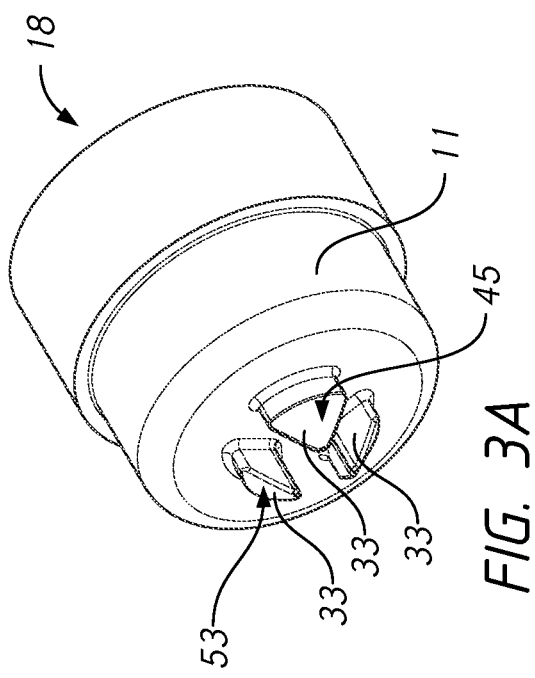
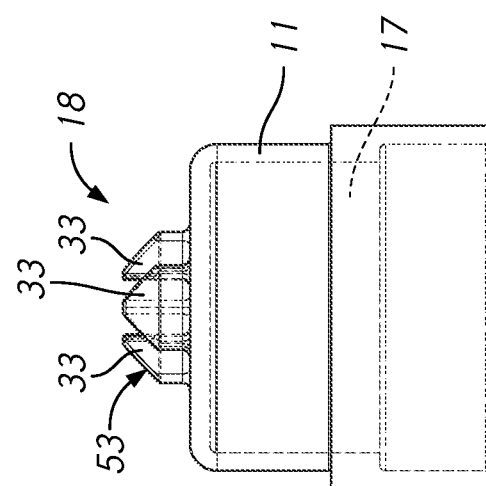
FIG. 3B
FIG. 3E
FIG. 3D
FIG. 3A
FIG. 3C

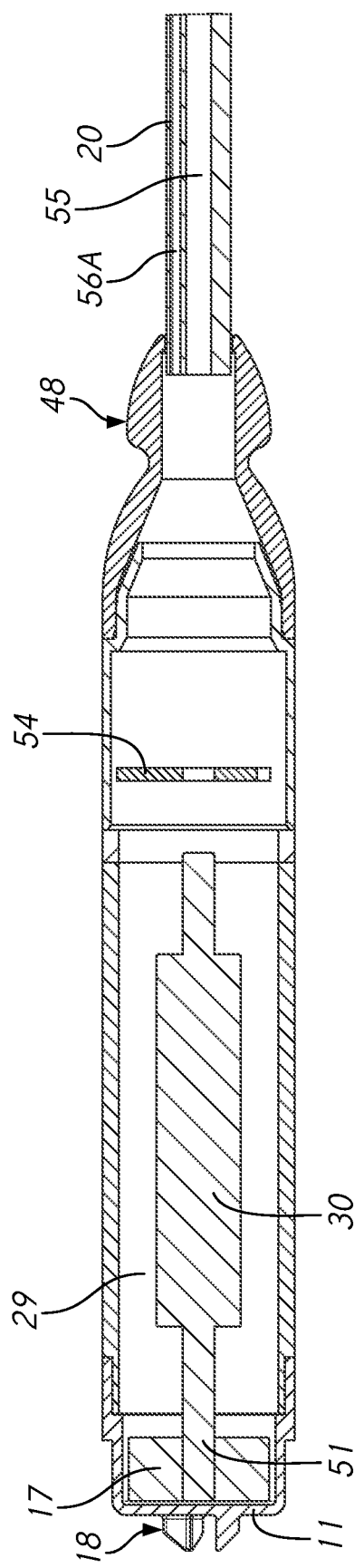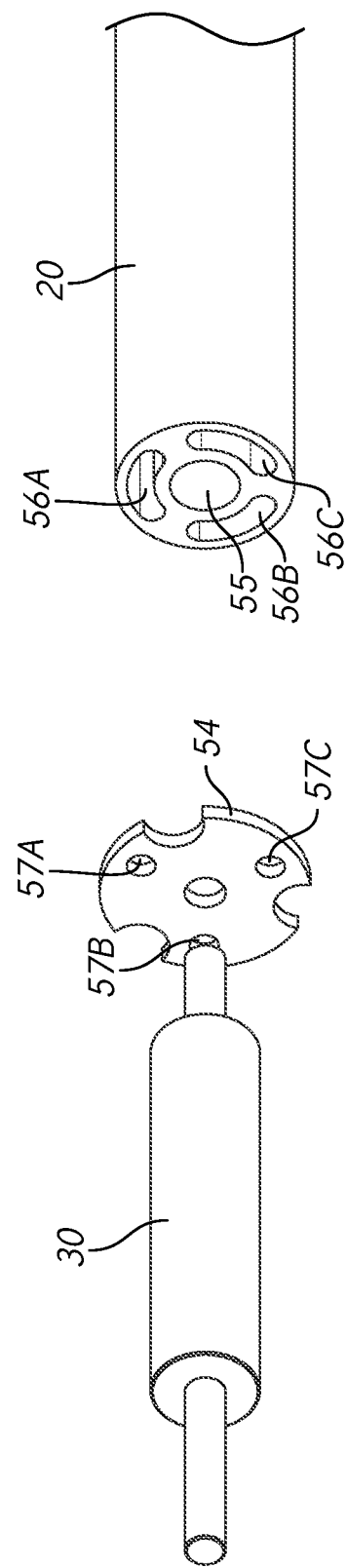
FIG. 8A
FIG. 8B
FIG. 8C

BLOOD PUMPS

INCORPORATION BY REFERENCE TO ANY PRIORITY APPLICATIONS

This application claims priority to U.S. application Ser. No. 17/535,303, filed Nov. 24, 2021, which is a continuation of International Application No. PCT/US2020/062928, filed Dec. 2, 2020, which claims priority to U.S. Provisional Patent Application No. 62/943,062, filed on Dec. 3, 2019, and to U.S. Provisional Patent Application No. 62/947,940, filed on Dec. 13, 2019, the entire contents of each of which are hereby incorporated by reference herein in their entirety and for all purposes. Any and all applications for which a foreign or domestic priority claim is identified in the Application Data Sheet as filed with the present application are hereby incorporated by reference under 37 C.F.R. § 1.57.

BACKGROUND

Field

This invention relates to improved blood pumps.

Description of the Related Art

In the field of cardiac assist devices and mechanical circulatory support, blood pumps are used to support the heart in circulating blood through the body. Implantable impeller pumps make up one common class of blood pumps used.

Impeller pumps use bearings to connect the impeller to the rest of the pump in a way that constrains the impeller both radially and axially, but leaves it free to rotate. Sleeve bearings (or journal bearings) are a common type of bearing that provide radial confinement. Cone bearings provide both axial and radial confinement. Both sleeve and cone bearings also have improved pressure-velocity characteristics (due to their two-dimensional bearing interfaces), in contrast to bearings that rely on point or line contact.

Blood pumps also typically include structure that provides torque coupling between the motor and the pump impeller. Common variations of this design element are direct torque coupling and magnetic torque coupling.

SUMMARY

There remains a continuing need for improved blood pumps.

One major difficulty with blood pumps is sensitivity of blood to the conditions created by the pump. Common problems include blood clots and hemolysis, especially with bearings that have areas where blood can stagnate and clot.

Key factors in the design and evaluation of blood pump comprise: enhancing fluid flow to the bearing regions, enhancing fluid flow from the bearing regions, creating lubricating fluid layers in the bearing regions, maintaining the pressure-volume characteristics of the bearing interfaces within favorable ranges, and minimizing forces on the blood that can lead to thrombosis or hemolysis.

In one embodiment, a modular bearing system for blood pumps is provided that enables different combinations of bearing design elements with unique and novel advantages. A first bearing is a sleeve bearing (or equivalently, a journal bearing) uniquely designed to allow flow through the pump with minimal obstruction. The other is a cone bearing. In some embodiments, one or more of these bearing designs may be used. In other embodiments, either bearing design may be used with additional bearing design(s). In other embodiments, the two bearing designs may be used together in a configuration that provides additional benefits.

The sleeve bearing may have a modified geometry for reduced thrombosis. Various low thrombosis sleeve geometries are considered. The sleeve bearings may contain added features (e.g. a thrust ring) that provide some degree of axial confinement as well as radial confinement.

The cone bearings described in this disclosure have modified geometries that promote full washing of the bearing surfaces by blood. The full washing of the bearing surfaces may be promoted by enhanced sourcing of blood to the bearing region, enhanced removal of blood from the bearing region, or some combination of these.

The sleeve bearing and the cone bearing may have certain features that support their combined use and offer unique advantages arising from these combinations.

In several embodiments, a blood flow assist system is disclosed. In some embodiments, the system consists essentially of an impeller assembly comprising a rotor assembly and an impeller coupled with the rotor assembly, the rotor assembly comprising a first curved bearing surface (e.g., a concave bearing surface), and a drive unit proximal the impeller assembly, the drive unit comprising a drive magnet and a drive bearing between the drive magnet and the impeller assembly, the drive bearing comprising a second curved bearing surface (e.g., a convex bearing surface) shaped to mate with (e.g., fit within) the first curved bearing surface. In some embodiments, the first curved bearing surface includes a fluid port. In some embodiments, the second bearing surface includes a void (e.g., a central hollow) and one or more channels extending radially outward from the void. The void can be in fluid communication with the fluid port so as to direct blood radially outward along the at least one channel. In some embodiments, the convex bearing surface has a distal end disposed distal of a proximal end of the rotor assembly. In some embodiments, the convex bearing surface comprises a plurality of distally-projecting segments, the plurality of distally-projecting segments spaced apart circumferentially to define at least one channel between adjacent segments.

In various illustrated embodiments, the rotor assembly can include a concave bearing surface, and the drive bearing can comprise a convex bearing surface. However, it should be appreciated that, in each of the embodiments disclosed herein, the rotor assembly may alternatively include a convex bearing surface and the drive bearing can comprise a concave bearing surface, with the convex bearing surface mating with (e.g., fitting within) the concave bearing surface. Further, in embodiments in which the rotor assembly comprises the convex bearing surface, the plurality of segments may extend proximally (e.g., as opposed to distally-extending) and can be spaced apart circumferentially to define at least one channel between adjacent segments.

In some embodiments, the rotor assembly comprises an impeller shaft and a rotor magnet coupled to the impeller shaft, the impeller disposed on the impeller shaft. In some embodiments, the impeller assembly comprises a second impeller disposed on the impeller shaft spaced apart proximally from the impeller along the impeller shaft. A flange can extend non-parallel from a proximal end portion of the impeller shaft, the second impeller comprising a plurality of vanes disposed on a generally proximally-facing surface of the flange.

In some embodiments, the impeller is configured to pump blood along a first flow pathway along an exterior surface of the impeller, a majority of the blood flowing along the first flow pathway being directed along a longitudinal axis of the blood flow assist system. In some embodiments, the system includes a second flow pathway through a lumen of the impeller shaft, the second impeller configured to direct blood from the second flow pathway radially outward relative to the longitudinal axis. In some embodiments, an angled cavity extends inwardly and distally relative to the generally proximally-facing surface of the flange. In some embodiments, the drive unit comprises a convex member sized to fit within the angled cavity. In some embodiments, the system includes a sleeve bearing disposed about the impeller shaft at a location distal the impeller. In some embodiments, in a cross-section taken perpendicular to an axis of rotation of the impeller, a support surface of the sleeve bearing is disposed about only a portion of a perimeter of the impeller shaft at a selected axial location, such that, when the impeller shaft is rotated about the axis of rotation, an exterior surface of the impeller shaft at the selected axial location is cyclically exposed to blood during operation of the blood flow assist system. In some embodiments, the system includes a pump housing, the impeller assembly disposed at least partially within the pump housing. In some embodiments, the pump housing includes an outlet, the outlet disposed proximal the impeller. In some embodiments, the second impeller is disposed proximal a distal end of the outlet. In some embodiments, the system includes a support structure coupled to or formed with the pump housing, the support structure comprising struts configured to contact a blood vessel wall to maintain spacing of the pump housing from a blood vessel wall in which the pump housing is disposed. In some embodiments, the blood flow assist system comprises a percutaneous pump configured for percutaneous insertion to a treatment location within a body of a patient. A motor can be mechanically coupled with the drive magnet and a power wire connected to the motor, the power wire extending proximally from the motor.

In several embodiments, a method of operating a blood flow assist system is disclosed. The method can include or consist essentially of percutaneously delivering an impeller assembly to a treatment location in a blood vessel of a patient, the impeller assembly comprising a rotor assembly and an impeller coupled with the rotor assembly, the rotor assembly comprising a concave bearing surface, the blood flow assist system comprising a drive unit proximal the impeller assembly, the drive unit comprising a drive magnet and a drive bearing between the drive magnet and the impeller assembly, the drive bearing comprising a convex bearing surface fitting within the concave bearing surface, the convex bearing surface comprising a plurality of distally-projecting segments, the plurality of distally-projecting segments spaced apart circumferentially to define at least one channel between adjacent segments; pumping blood longitudinally along a length of the impeller assembly and radially outwardly through the at least one channel; and removing the impeller assembly from the patient. In some embodiments, the method includes directing blood radially outward between the drive unit and a second impeller disposed proximal the impeller, the drive unit having a distal end disposed distal of a proximal end of the second impeller. In some embodiments, the method includes providing relative motion between the impeller assembly and a sheath to cause a plurality of struts to self-expand radially outwardly to engage a wall of the blood vessel. In some embodiments, providing opposite relative motion between the impeller assembly and the sheath to cause the plurality of struts to collapse within the sheath. In some embodiments, the rotor assembly comprises an impeller shaft on which the impeller is disposed and a sleeve bearing disposed about the impeller shaft distal the impeller, the method comprising cyclically exposing an exterior surface of the impeller shaft to blood at a selected axial location. In some embodiments, the method includes supplying electrical current to a motor by way of a power wire, the motor being operably connected to the impeller assembly, the power wire extending outside a body of the patient.

In several embodiments, a method of manufacturing a blood flow assist system is disclosed. In some embodiments, the method includes or consists essentially of providing an impeller assembly comprising a rotor assembly and an impeller coupled with the rotor assembly, the rotor assembly comprising a concave bearing surface; and providing a drive unit proximal the impeller assembly, the drive unit comprising a drive magnet and a drive bearing between the drive magnet and the impeller assembly, the drive bearing comprising a convex bearing surface shaped to fit within the concave bearing surface, the convex bearing surface having a distal end disposed distal of a proximal end of the rotor assembly.

In some embodiments, providing the drive unit comprises forming a plurality of distally-projecting segments in the convex bearing surface, the plurality of distally-projecting segments spaced apart circumferentially to define at least one channel between adjacent segments. In some embodiments, the method comprises at least partially disposing the impeller in a pump housing. In some embodiments, the method comprises providing a support structure to be coupled to or formed with the pump housing, the support structure comprising struts configured to contact a blood vessel wall to maintain spacing of the pump housing from a blood vessel wall in which the pump housing is disposed. In some embodiments, the method comprises providing a motor proximal the impeller, the motor configured to impart rotation to the impeller. In some embodiments, the method comprises connecting the motor to a power wire that extends proximally relative to the motor.

In several embodiments, a blood flow assist system is disclosed. In some embodiments, the blood flow assist system includes or consists essentially of an impeller assembly comprising an impeller shaft, a first impeller disposed on the impeller shaft, and a second impeller disposed on the impeller shaft spaced apart proximally from the first impeller along the impeller shaft; and a drive unit configured to impart rotation to the impeller shaft, the drive unit having a distal end disposed distal a proximal end of the second impeller. In some embodiments, the first impeller is configured to pump blood along a first flow pathway along an exterior surface of the first impeller, a majority of the blood flowing along the first flow pathway being directed along a longitudinal axis of the blood flow assist system. In some embodiments, the system includes a fairing disposed about the impeller shaft between the first impeller and the second impeller, the first flow pathway disposed along an angled exterior surface of the fairing. In some embodiments, the system includes a second flow pathway through a lumen of the impeller shaft, the second impeller configured to direct blood from the second flow pathway radially outward relative to the longitudinal axis. In some embodiments, during operation of the blood flow assist system, blood pumped along the second flow pathway flows between a proximal end portion of the impeller shaft and the distal end of the drive unit.

In some embodiments, the drive unit comprises a drive magnet and a drive bearing between the drive magnet and the impeller assembly, the drive bearing comprising a convex bearing surface having a plurality of distally-projecting segments, the plurality of distally-projecting segments spaced apart circumferentially to define at least one channel between adjacent segments, the secondary flow pathway comprising the at least one channel. In some embodiments, the system includes a flange extending non-parallel from a proximal end portion of the impeller shaft, the second impeller disposed comprising a plurality of vanes on a generally proximally-facing surface of the flange. In some embodiments, the system includes an angled cavity extending inwardly and distally relative to the generally proximally-facing surface of the flange. In some embodiments, the drive unit comprises a convex member sized to fit within the angled cavity. In some embodiments, the system includes a rotor magnet coupled to the impeller shaft, the rotor magnet disposed adjacent a distally-facing surface of the flange. In some embodiments, the system includes a sleeve bearing disposed about the impeller shaft at a location distal the first impeller. In some embodiments, in a cross-section taken perpendicular to an axis of rotation of the first impeller, a support surface of the sleeve bearing is disposed about only a portion of a perimeter of the impeller shaft at a selected axial location, such that, when the impeller shaft is rotated about the axis of rotation, an exterior surface of the impeller shaft at the selected axial location is cyclically exposed to blood during operation of the blood flow assist system. In some embodiments, the system includes a pump housing, the impeller assembly disposed at least partially within the pump housing. In some embodiments, the pump housing includes an outlet, the outlet disposed proximal the first impeller. In some embodiments, the second impeller is disposed proximal a distal end of the outlet. In some embodiments, the system includes a support structure coupled to or formed with the pump housing, the support structure comprising struts configured to contact a blood vessel wall to maintain spacing of the pump housing from a blood vessel wall in which the pump housing is disposed. In some embodiments, the first impeller comprises a plurality of outwardly-extending, axially-aligned blades. In some embodiments, a kit includes the blood flow assist system that comprises a motor assembly configured to impart rotation to the first impeller and the second impeller and a power wire electrically connected to the motor assembly. The kit can include a console configured to electrically connect to the power wire. In some embodiments, the impeller shaft, the second impeller, and the flange form an integrated rotor core, the first impeller attached to the impeller shaft. In some embodiments, the impeller shaft, the first impeller, the second impeller, and the flange form a unitary body.

In several embodiments, a blood pump is disclosed. In some embodiments, the blood pump includes or consists essentially of a primary impeller, a flow tube routed through the primary impeller, a rotatable piece comprising a secondary impeller, a conical opening, and the flow tube, and a drive unit sealed by a drive unit cover, the drive unit cover comprising a conical member that matches the contour of and fits inside the conical opening. In some embodiments, the drive unit comprises a magnet sealed in the drive unit cover. In some embodiments, the drive unit comprises a motor, the magnet rotatable by the motor. In some embodiments, the secondary impeller comprises a plurality of vanes.

In several embodiments, a method of operating a blood flow assist system is disclosed. In some embodiments, the method includes or consists essentially of percutaneously delivering an impeller assembly to a treatment location in a blood vessel of a patient, the impeller assembly comprising an impeller shaft, a first impeller disposed on the impeller shaft, and a second impeller disposed on the impeller shaft spaced apart proximally from the first impeller along the impeller shaft; pumping blood along a first flow pathway and a second flow pathway, the first flow pathway disposed along an exterior surface of the first impeller, a majority of the blood flowing along the first flow pathway being directed along a longitudinal axis of the blood flow assist system, the second flow pathway disposed through a lumen of the impeller shaft, the second impeller directing blood from the second flow pathway radially outward relative to the longitudinal axis; and removing the blood flow assist system from the patient. In some embodiments, the method comprises directing blood radially outward between the second impeller and a drive unit, the drive unit having a distal end disposed distal of a proximal end of the second impeller. In some embodiments, the method comprises providing relative motion between the impeller assembly and a sheath to cause a plurality of struts to self-expand radially outwardly to engage a wall of the blood vessel. In some embodiments, the method comprises providing opposite relative motion between the impeller assembly and the sheath to cause the plurality of struts to collapse within the sheath. In some embodiments, a sleeve bearing is disposed about the impeller shaft distal the first impeller, the method comprising cyclically exposing an exterior surface of the impeller shaft to blood at a selected axial location. In some embodiments, the method comprises supplying electrical current to a motor by way of a power wire, the motor being operably connected to the impeller assembly, the power wire extending outside a body of the patient.

In several embodiments, a method of manufacturing a blood flow assist system is disclosed. In some embodiments, the method includes or consists essentially of mounting a first impeller on an impeller shaft, a flange disposed at a proximal end of the impeller shaft; and providing a second impeller spaced apart proximally from the first impeller along the impeller shaft, the second impeller disposed on a proximally-facing surface of the flange. In some embodiments, the method comprises at least partially disposing the first impeller and the second impeller in a pump housing. In some embodiments, the method comprises providing a support structure to be coupled to or formed with the pump housing, the support structure comprising convex contact pads configured to contact a blood vessel wall to maintain spacing of the pump housing from a blood vessel wall in which the pump housing is disposed. In some embodiments, the method comprises comprising providing a motor proximal the second impeller, the motor configured to impart rotation to the impeller shaft. In some embodiments, the method comprises connecting the motor to a power wire that extends proximally relative to the motor, the motor sized to be inserted into a patient's vasculature and the power wire configured to extend through the vasculature to a location outside the patient's body.

In several embodiments, a blood flow assist system is provided. In some embodiments, the system comprises or consists essentially of an impeller (or first impeller), a lumen extending through the first impeller along a longitudinal axis of the first impeller, a primary flow pathway along an exterior surface of the first impeller, and a secondary flow pathway along the lumen. In some embodiments, the system includes an impeller assembly comprising an impeller shaft with the impeller disposed on the impeller shaft, the impeller shaft including the lumen extending from a distal end of the impeller shaft to a proximal end of the impeller shaft. In some embodiments, a drive unit configured to impart rotation to the impeller shaft and the impeller is provided, at least a portion of the drive unit positioned proximal the proximal end of the impeller shaft. In one embodiment, during operation of the blood flow assist system, blood is pumped proximally along the primary flow pathway and the secondary flow pathway. In some embodiments, the blood flow assist system includes a pump housing. In one embodiment, the primary flow pathway is disposed between the exterior surface of the first impeller and the pump housing is also provided. For example, the primary flow pathway can be disposed between (and extend from) a radially outermost surface of the first impeller to an internal wall of the pump housing. In one embodiment, during operation of the blood flow assist system, blood pumped along the secondary flow pathway flows between the proximal end of the impeller shaft and the drive unit. In one embodiment, the drive unit comprises a drive magnet and a drive bearing between the drive magnet and the impeller assembly, the drive bearing comprising a convex bearing surface having a plurality of distally-projecting segments, the plurality of distally-projecting segments spaced apart circumferentially to define at least one channel between adjacent segments, the secondary flow pathway comprising the at least one channel. In some embodiments, a second impeller is disposed on the impeller shaft spaced apart proximally from the first impeller along the impeller shaft. The blood flow assist system can include a flange at a proximal end of the impeller shaft, the second impeller disposed on a proximally-facing surface of the flange. In some embodiments, the impeller shaft, the second impeller, and the flange form an integrated rotor core, the first impeller attached to the impeller shaft. In some embodiments, the impeller shaft, the first impeller, the second impeller, and the flange form a unitary body. In some embodiments, during operation of the blood flow assist system, blood pumped along the secondary flow pathway flows between a proximal end of the impeller shaft and the drive unit. In some embodiments, a kit can include the blood flow assist system that further includes a motor assembly configured to impart rotation to the impeller and a power wire electrically connected to the motor assembly. The kit can include a console configured to electrically connect to the power wire.

In several embodiments, a blood flow assist system is disclosed. In some embodiments, the blood flow assist system includes or consists essentially of a pump housing; an impeller assembly disposed in the pump housing, the impeller assembly comprising an impeller shaft and an impeller on the impeller shaft, the impeller shaft configured to rotate about an axis of rotation; and a sleeve bearing disposed about the impeller shaft distal the impeller. In some embodiments, the sleeve bearing has an inner support structure supporting the impeller shaft, an outer support structure coupled to or formed with the pump housing, and a connecting structure extending radially between the inner support structure and the outer support structure. In some embodiments, the inner support structure comprises a distal boundary, the distal boundary angled relative to the axis of rotation such that, in a cross-section taken perpendicular to the axis of rotation, only a portion of the distal boundary is disposed about the impeller shaft at a selected axial location along the axis of rotation, such that, when the impeller shaft is rotated about the axis of rotation, an exterior surface of the impeller shaft at the selected axial location is cyclically exposed to blood during operation of the blood flow assist system. In some embodiments, in a cross-section taken perpendicular to the axis of rotation, a support surface of the sleeve bearing is disposed about only a portion of a perimeter of the impeller shaft at a selected axial location along the axis of rotation, such that, when the impeller shaft is rotated about the axis of rotation, an exterior surface of the impeller shaft at the selected axial location is cyclically exposed to blood during operation of the blood flow assist system. In some embodiments, at all axial locations along the axis of rotation along a length of the sleeve bearing, the support surface of the sleeve bearing is disposed only partially about the perimeter of the impeller shaft. In some embodiments, at an axial location along the axis of rotation, a support surface of the sleeve bearing is disposed only partially about a perimeter of the impeller shaft. In some embodiments, the system includes a drive unit configured to impart rotation to the impeller shaft, wherein the drive unit comprises a drive magnet and a drive bearing between the drive magnet and the impeller assembly, the drive bearing comprising a convex bearing surface and a plurality of distally-projecting segments extending from the convex bearing surface, the plurality of distally-projecting segments spaced apart circumferentially to define at least one channel between adjacent segments.

In some embodiments, the support surface comprises a crenulated surface as shown in a side view of the sleeve bearing. In some embodiments, the support surface is disposed completely about the perimeter of the impeller shaft at a second axial location along the axis of rotation. In some embodiments, the system includes a pump housing, the impeller assembly disposed in the pump housing. In some embodiments, the system includes a support structure coupled with the pump housing, the support structure comprising struts configured to contact a blood vessel wall to maintain spacing of the pump housing from a blood vessel wall in which the pump housing is disposed. In some embodiments, the impeller is configured to pump blood along a first flow pathway along an exterior surface of the impeller, a majority of the blood flowing along the first flow pathway being directed along the axis of rotation. In some embodiments, the system includes a second impeller disposed on the impeller shaft spaced apart proximally from the impeller along the impeller shaft, the second impeller configured to direct blood radially outward relative to the axis of rotation from a second flow pathway in a lumen of the impeller shaft. In some embodiments, the system includes a flange extending non-parallel from a proximal end portion of the impeller shaft, the second impeller disposed on a generally proximally-facing surface of the flange. In some embodiments, a kit includes the blood flow assist system that comprises a motor assembly configured to impart rotation to the impeller and a power wire electrically connected to the motor assembly. The kit can include a console configured to electrically connect to the power wire.

In several embodiments, a blood pump is disclosed. In some embodiments, the blood pump includes or consists essentially of a pump rotor comprising a primary impeller and a rotating member including a flow tube that rotates the primary impeller about an axis of rotation; and a sleeve bearing that fits around the pump rotor, the sleeve bearing comprising a bearing interface edge non-perpendicular to the axis of rotation. In some embodiments, the bearing interface edge comprises a non-circular sleeve edge that ensures that there are no points on the rotating member that remain aligned with the sleeve edge throughout rotation of the rotating member. In some embodiments, the sleeve bearing exposes at least one point on the rotating member throughout an entire height of the sleeve bearing so that a surface of the rotating member is only covered by the sleeve bearing for a portion of rotation. In some embodiments, the bearing interface edge comprises an ellipse. In some embodiments, the bearing interface edge varies in a sinusoidal manner.

In several embodiments, a method of operating a blood flow assist system is disclosed. In some embodiments, the method includes or consists essentially of percutaneously delivering an impeller assembly to a treatment location in a blood vessel of a patient, the impeller assembly disposed in the pump housing, the impeller assembly comprising an impeller shaft and an impeller on the impeller shaft, the impeller shaft configured to rotate about an axis of rotation, a sleeve bearing disposed about the impeller shaft; pumping blood through the blood flow assist system such that an exterior surface of the impeller shaft is cyclically exposed to blood at a selected axial location; and removing the impeller assembly from the patient. In some embodiments, at the selected axial location along the axis of rotation, a support surface of the sleeve bearing is disposed only partially about a perimeter of the impeller shaft. In some embodiments, the method includes directing blood longitudinally along a length of the impeller assembly and radially outwardly between a drive unit and a second impeller disposed proximal the impeller, the drive unit having a distal end disposed distal of a proximal end of the second impeller. In some embodiments, the method includes retracting a sheath to cause a plurality of struts to self-expand radially outwardly to engage a wall of the blood vessel.

In several embodiments, a method of manufacturing a blood flow assist system is disclosed. In some embodiments, the method includes or consists essentially of disposing an impeller assembly disposed in a pump housing, the impeller assembly comprising an impeller shaft and an impeller on the impeller shaft, the impeller shaft configured to rotate about an axis of rotation; and disposing a sleeve bearing about the impeller shaft, wherein, at an axial location along the axis of rotation, a support surface of the sleeve bearing is disposed only partially about a perimeter of the impeller shaft. In some embodiments, the method includes providing a drive unit proximal the impeller assembly, the drive unit comprising a drive magnet and a drive bearing between the drive magnet and the impeller assembly, the drive bearing comprising a convex bearing surface shaped to fit within the concave bearing surface. In some embodiments, providing the drive unit comprises forming a plurality of distally-projecting segments in the convex bearing surface, the plurality of distally-projecting segments spaced apart circumferentially to define at least one channel between adjacent segments. In some embodiments, the method includes providing a support structure to be coupled to or formed with the pump housing, the support structure comprising struts configured to contact a blood vessel wall to maintain spacing of the pump housing from a blood vessel wall in which the pump housing is disposed. In some embodiments, the method includes providing a motor proximal the impeller, the motor configured to impart rotation to the impeller. In some embodiments, the method includes connecting the motor to a power wire that extends proximally relative to the motor.

In several embodiments, a blood flow assist system is disclosed. The system can include or consist essentially of an impeller assembly comprising an impeller shaft, an impeller on the impeller shaft, a primary flow pathway disposed along an exterior surface of the impeller, a rotor assembly at a proximal portion of the impeller shaft, the rotor assembly comprising a concave bearing surface, a flange disposed about the concave bearing surface, a rotor magnet supported by the impeller shaft, and a second impeller disposed on a proximally-facing surface of the flange, wherein a secondary flow pathway is disposed along a lumen of the impeller shaft, and wherein, during operation of the blood flow assist system, blood is pumped proximally along the primary flow pathway and the secondary flow pathway; a sleeve bearing distal the impeller, the sleeve bearing disposed about the impeller shaft such that, during rotation of the impeller shaft, an exterior surface of the impeller shaft at a selected axial location is cyclically exposed to blood during operation of the blood flow assist system; and a drive unit having a distal end disposed distal a proximal end of the second impeller, the drive unit comprising a drive magnet and a drive bearing between the drive magnet and the impeller assembly, the drive bearing comprising a convex bearing surface shaped to fit within the concave bearing surface and a plurality of distally-projecting segments, the plurality of distally-projecting segments spaced apart circumferentially to define at least one channel between adjacent segments, wherein the drive unit is configured to cause the drive magnet to impart rotation to the rotor magnet and the impeller shaft. In some embodiments, a kit includes the blood flow assist system that comprises a motor assembly configured to impart rotation to the impeller and a power wire electrically connected to the motor assembly. The kit can include a console configured to electrically connect to the power wire. In some embodiments, the blood flow assist system comprises a percutaneous pump configured for percutaneous insertion to a treatment location within a body of a patient.

In several embodiments, a blood flow assist system is disclosed. In some embodiments, the blood flow assist system includes or consists essentially of a pump configured for percutaneous insertion to a treatment location of a patient; an elongate body extending proximally from the pump; and a retrieval feature between a proximal curved portion of the pump and the elongate body, the retrieval feature comprising an enlarged diameter section and a neck between the enlarged diameter section and the proximal curved portion of the pump. In some embodiments, the enlarged diameter section comprises a first curved portion having a first radius of curvature and a second curved portion having a second radius of curvature different from the first radius of curvature. In some embodiments, a first plane extending parallel to a longitudinal axis of the blood flow assist system and intersecting the first curved portion defines a first angle between the proximal curved portion and the first curved portion, and a second plane extending parallel to the longitudinal axis and intersecting the second curved portion defines a second angle between the proximal curved portion and the second curved portion, the second angle different from the first angle. In some embodiments, the enlarged diameter section comprises a plurality of lobes extending radially outward. In some embodiments, the pump comprises a pump head and a motor housing coupled with the pump head, a proximal end portion of the motor housing comprising the proximal curved portion. In some embodiments, the pump head comprises a pump housing and an impeller in the pump housing, and wherein the motor housing includes a motor operably coupled with the impeller. In some embodiments, the neck comprises a first depth at a first circumferential position of the retrieval feature and a second depth less than the first depth at a second circumferential position of the retrieval feature spaced apart from the first circumferential position.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 1B is a schematic perspective view of a pump at a distal portion of the blood flow assist system of FIG. 1A.

FIG. 1C is a schematic perspective, partially-exploded view of the pump of FIG. 1B.

FIG. 3A is a schematic perspective view of a drive bearing according to various embodiments.

FIG. 3B is a front end view of the drive bearing of FIG. 3A.

FIG. 3C is a side view of the drive bearing of FIG. 3A.

FIG. 3D is a schematic front end view of a drive bearing according to another embodiment.

FIG. 3E is a schematic front end view of a drive bearing according to another embodiment.

FIG. 8A is a schematic side sectional view of a motor housing according to various embodiments.

FIG. 8B is a schematic perspective view of a motor and a motor mount support.

FIG. 8C is a schematic perspective view of a distal end of a power wire configured to supply power to the motor.

DETAILED DESCRIPTION

Figure 1A:
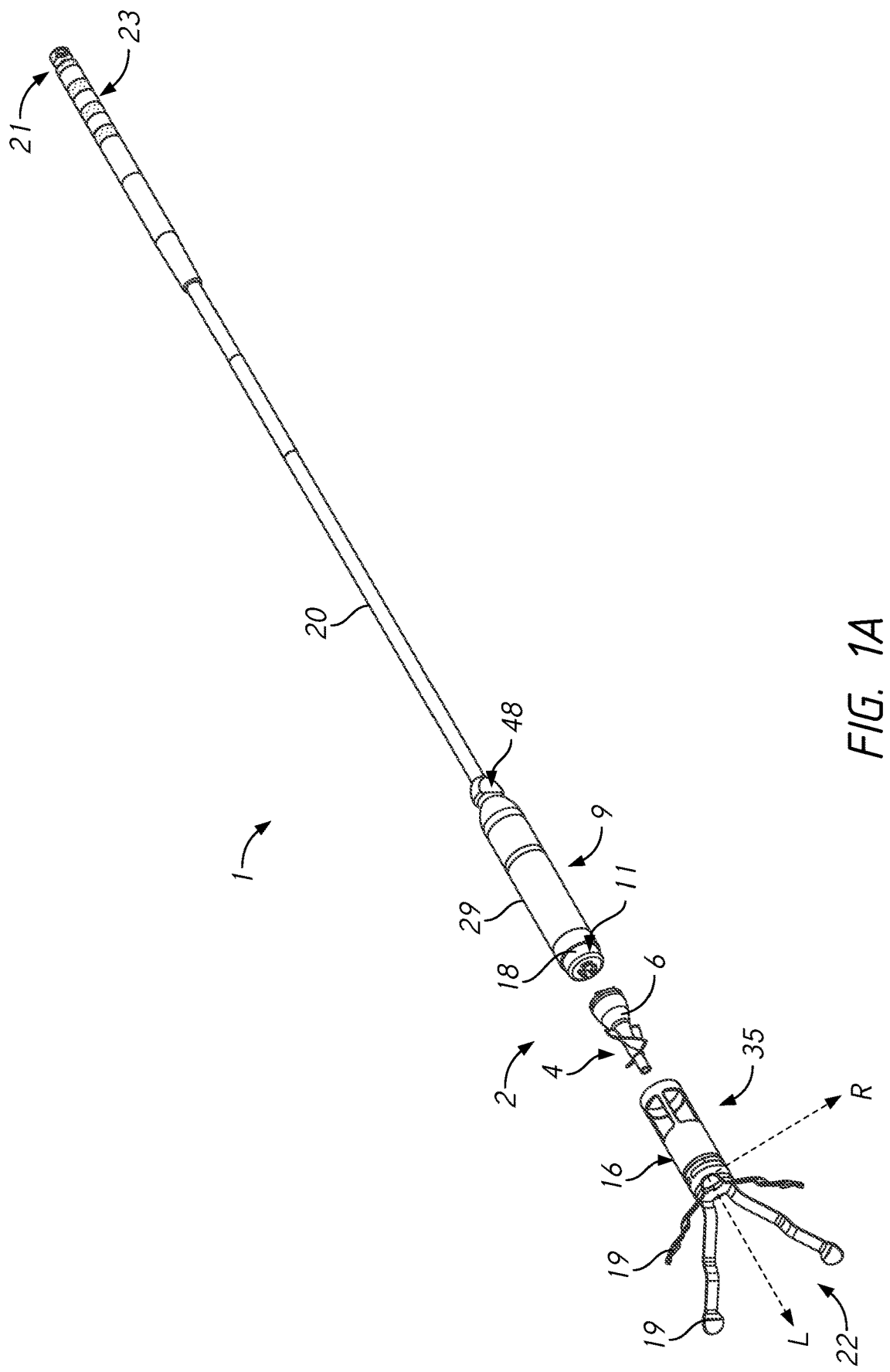
FIG. 1A is a schematic perspective, partially-exploded view of a blood flow assist system, according to various embodiments.

Refer now to the drawings wherein depicted elements are not necessarily shown to scale and wherein like or similar elements are designated by the same reference numeral through the several views. Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

I. Overview of Blood Flow Assist Systems

Various embodiments disclosed herein relate to a blood flow assist system 1 configured to provide circulatory support to a patient, as illustrated in FIGS. 1A-1D. The system 1 can be sized for intravascular delivery to a treatment location within the circulatory system of the patient, e.g., to a location within the descending aorta of the patient. As shown in FIG. 1A, the system 1 can have a proximal end 21 with a connector 23 configured to connect to an external control system, e.g., a console (not shown). The connector 23 can provide electrical communication between the control system and a power wire 20 extending distally along a longitudinal axis L from the connector 23 and the proximal end 21. The power wire 20 can comprise an elongate body that electrically and mechanically connects to a pump 2 at or near a distal end 22 of the blood flow assist system 1, with the distal end 22 spaced apart from the proximal end 21 along the longitudinal axis L.

Figure 1D:
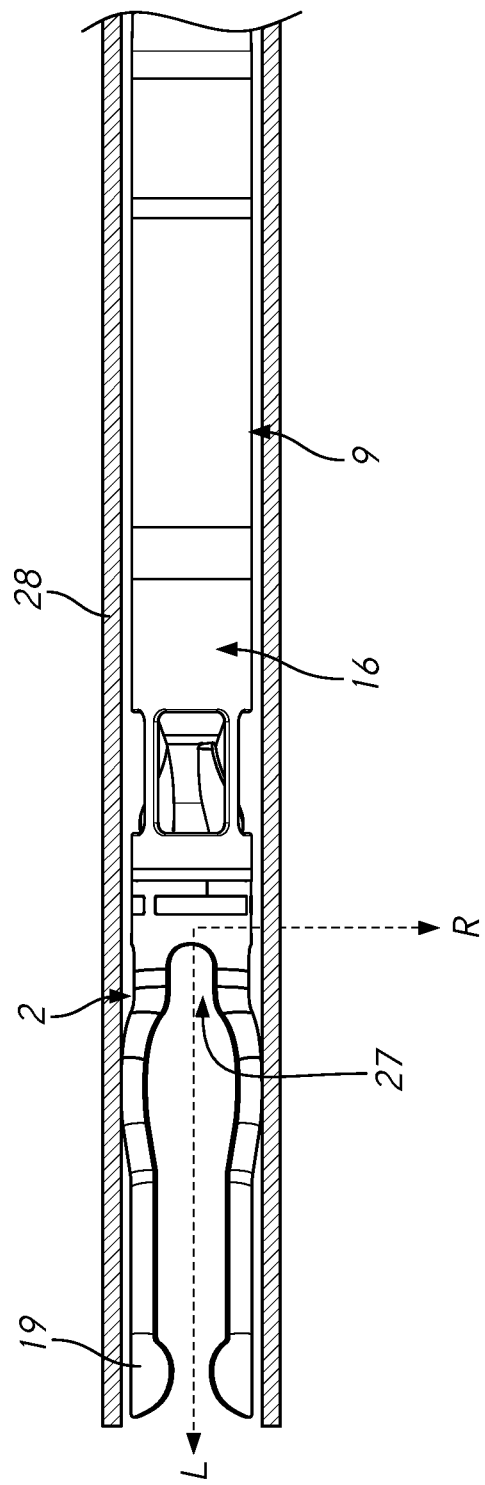
FIG. 1D is a schematic side view of the pump disposed in a collapsed configuration in a delivery sheath.
Figure 1E:
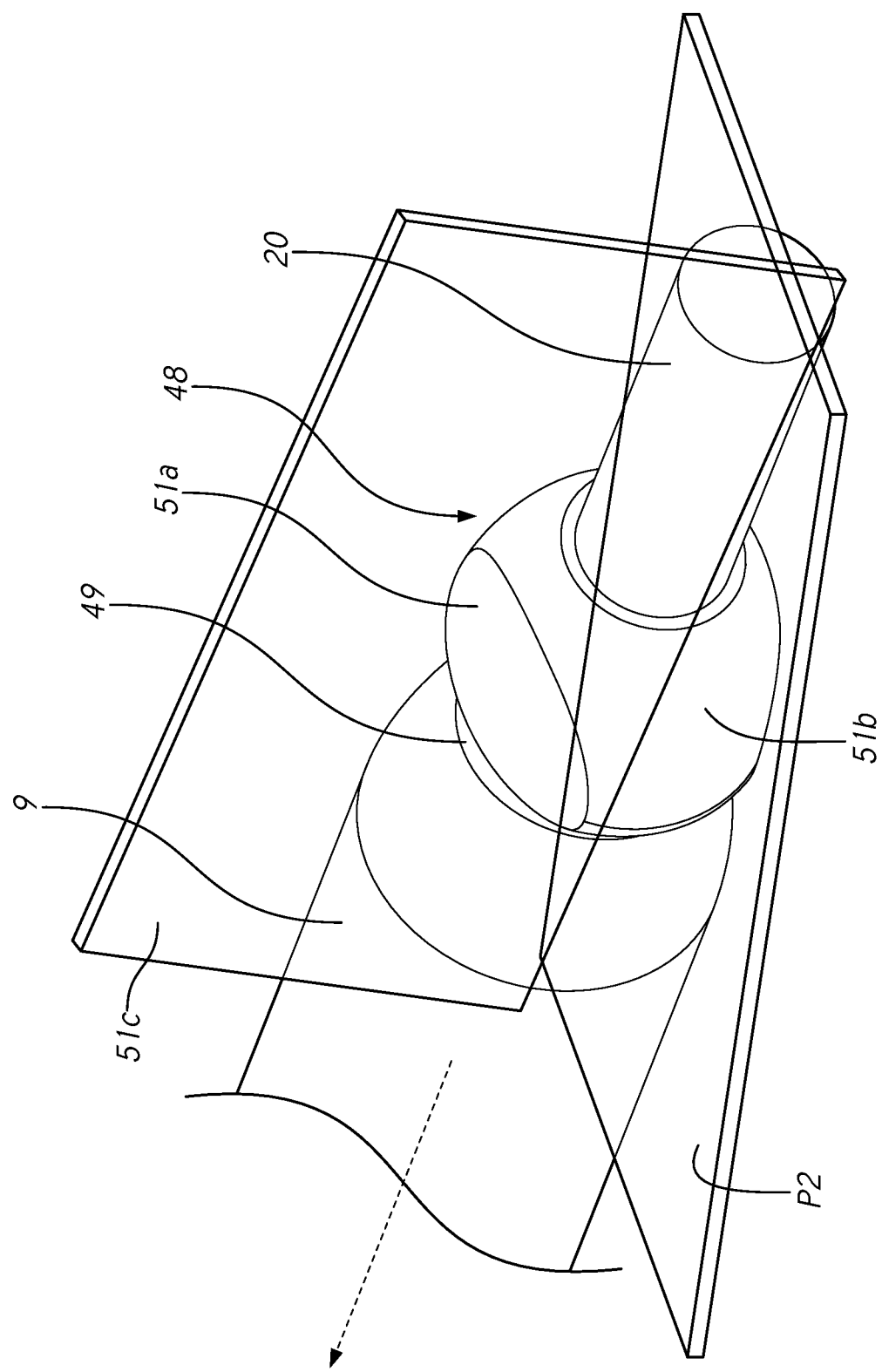
FIG. 1E is a schematic perspective view of a retrieval feature used to remove the pump, according to some embodiments.

The pump 2 can comprise a pump head 50 including a pump housing 35 connected to a drive unit 9 that includes a motor housing 29. A retrieval feature 48 can be provided at a proximal end portion of the pump 2. In some embodiments, the retrieval feature can be coupled with the distal end of the power wire 20 between the power wire 20 and the motor housing 29. After a procedure, the clinician can remove the pump 2 from the patient by engaging a tool (e.g., a snare, clamp, hook, etc.) with the retrieval feature 48 to pull the pump 2 from the patient. For example, the retrieval feature 48 can comprise a neck 49 (e.g., a reduced diameter section) at a proximal curved portion 51c of the motor housing 29 and an enlarged diameter section disposed proximal the neck 49. The enlarged diameter section can comprise a first curved portion 51a and a second curved portion 51b, as shown in FIG. 1E. The first and second curved portions 51a, 51b can comprise convex surfaces, e.g., convex ball portions. The first and second curved portions 51a, 51b can have different radii of curvature. For example, as shown in FIG. 1E, the first curved portion 51a can have a larger radius of curvature than the second curved portion 51b. The first curved portion 51a can be disposed on opposing sides of the retrieval feature 48 in some embodiments. The second curved portion 51b can be disposed around the first curved portion 51a and can have a radially-outward facing surface and a proximally-facing convex surface coupled to the distal end of the power wire 20. The neck 49 can have a first depth at a first circumferential position of the retrieval feature 48 and a second depth less than the first depth at a second circumferential position of the retrieval feature 48 spaced apart from the first circumferential position.

Beneficially, as shown in FIG. 1E, one or more first planes P1 extending parallel to the longitudinal axis L and intersecting the first curved portion 51a can have a first angle or taper between the proximal curved portion 51c of the motor housing 29 and the first curved portion 51a. One or more second planes P2 extending parallel to the longitudinal axis L and intersecting the second curved portion 51b can have a second angle or taper (which is different from the first angle or taper) between the proximal curved portion 51c of the motor housing 29 and the second curved portion 51b. The first angle or taper can provide a gradual, continuous (generally monotonically decreasing) geometric transition between the proximal curved portion 51c of the motor housing 29 and the power wire 20, which can provide for smooth blood flow and reduce the risk of thrombosis. The second curved portion 51b can serve as a lobe that extends radially outward, e.g., radially farther out than the first curved portion 51a. The second curved portion 51b can be used to engage with a retrieval device or snare to remove the pump 2 from the anatomy. Some cross sections through the longitudinal axis of the retrieval feature 48 can contain a substantial neck (e.g., a local minimum in the radius of curvature measured along its central axis) while other cross sections through the longitudinal axis of the retrieval feature 48 can contain an insubstantial local minimum or no local minimum. In the illustrated embodiment, there are two first curved portions 51a that can serve as a dual lobe retrieval feature. In other embodiments, more or fewer lobes can be provided to enable pump retrieval while ensuring smooth flow transitions between the motor housing 29 and power wire 20.

As shown in FIGS. 1B-1C and 1E, the neck 49 can be disposed between the curved portions 51a, 51b and the proximally-facing convex surface 51c of the motor housing 29. In the illustrated embodiment, the retrieval feature 48 can be coupled to or integrally formed with the motor housing 29. In other arrangements, the retrieval feature 48 can be disposed at other locations of the pump 2. As shown, the retrieval feature 48 can be symmetrical and continuously disposed about the longitudinal axis L. In other arrangements, the retrieval feature 48 can comprise a plurality of discrete surfaces spaced apart circumferentially and/or longitudinally.

In the illustrated embodiments, the motor housing 29 (and motor) can be part of the pump 2 and disposed inside the vasculature of the patient in use. In other embodiments, however, the motor housing 29 (and motor) can be disposed outside the patient and a drive cable can connect to the impeller 6.

As shown in FIGS. 1A-1C, the drive unit 9 can be configured to impart rotation to an impeller assembly 4 disposed in the pump housing 35 of the pump head 50. As explained herein, the drive unit 9 can include a drive magnet 17 and a motor 30 (see FIGS. 6-8A) disposed in the motor housing 29 capped by a distal drive unit cover 11. The drive unit cover 11 can be formed with or coupled to a drive bearing 18. The drive magnet 17 can magnetically couple with a corresponding driven or rotor magnet 12 (see FIG. 7) of the impeller assembly 4 that is disposed within the shroud 16 proximal the impeller 6. The power wire 20 can extend from the treatment location to outside the body of the patient, and can provide electrical power (e.g., electrical current) and/or control to the motor 30. Accordingly, no spinning drive shaft extends outside the body of the patient in some embodiments. As explained herein, the power wire 20 can energize the motor 12, which can cause the drive magnet 17 to rotate about the longitudinal axis L, which can serve as or be aligned with or correspond to an axis of rotation. Rotation of the drive magnet 17 can impart rotation of the rotor magnet 12 and a primary or first impeller 6 of the impeller assembly 4 about the longitudinal axis L. For example, as explained herein, the rotor magnet 12 can cause an impeller shaft 5 (which can serve as a flow tube) to rotate which, in turn, can cause the first impeller 6 to rotate to pump blood. In other embodiments, the drive unit 9 can comprise a stator or other stationary magnetic device. The stator or other magnetic device can be energized, e.g., with alternating current, to impart rotation to the rotor magnet 12. In the illustrated embodiments, the impeller 6 can have one or a plurality of blades 40 extending radially outward along a radial axis R that is radially transverse to the longitudinal axis L. For example, the first impeller 6 can have a plurality of (e.g., two) axially-aligned blades 40 that extend radially outwardly from a common hub and that have a common length along the longitudinal axis L. The curvature and/or overall profile can be selected so as to improve flow rate and reduce shear stresses. Skilled artisans would appreciate that other designs for the first impeller 5 may be suitable.

As shown in FIGS. 1A-1C, the impeller assembly 4 can be disposed in a shroud 16. The impeller shaft 5 can be supported at a distal end by a sleeve bearing 15 connected to a distal portion of the shroud 16. A support structure such as a localization system can comprise a base portion 36 coupled with the sleeve bearing 15 and/or the shroud 16. In some embodiments, the base portion 36, the sleeve bearing 15, and/or the shroud 16 can be welded together. The base portion 36 of the support structure or localization system, the sleeve bearing 15, and the shroud 16 can cooperate to at least partially define the pump housing 35, as shown in FIGS. 1A and 1C. The localization system can comprise a plurality of self-expanding struts 19 having convex contact pads 24 configured to contact a blood vessel wall to maintain spacing of the pump housing 35 from the blood vessel wall in which the pump housing 35 is disposed. In FIGS. 1A-1C, the struts 19 of the localization system are illustrated in an expanded, deployed configuration, in which the contact pads 24 extend radially outward to a position in which the contact pads 24 would contact a blood vessel wall within which the pump 2 is disposed to at least partially control position and/or orientation of, e.g., to anchor, the pump 2 during operation of the system 1.

A first fluid port 27 can be provided distal the impeller assembly 4 at a distal end of the pump housing 35. The shroud 16 can comprise a proximal ring 26 coupled with the motor housing 29 and a plurality of second fluid ports 25 formed in a proximal portion of the shroud 16 adjacent (e.g., immediately distal) the proximal ring 26. As shown in FIG. 1C, the second fluid ports 25 can comprise openings formed between axially-extending members 60 that extend along the longitudinal axis L between the proximal ring 26 and a cylindrical section 59 of the shroud 16. In some embodiments, the axially-extending members 60 (also referred to as pillars) can be shaped to serve as vanes that can shape or direct the flow of blood through the second fluid ports 25. For example, in various embodiments, the axially-extending members 60 can be angled or curved to match the profile of the impeller blades 40. In other embodiments, the axially-extending members 60 may not be angled to match the blades 40. In some embodiments, the first fluid port 27 can comprise an inlet port into which blood flows. In such embodiments, the impeller assembly 4 can draw blood into the first fluid port 27 and can expel the blood out of the pump 2 through the second fluid ports 25, which can serve as outlet ports. In other embodiments, however, the direction of blood flow may be reversed, in which case the second fluid ports 25 may serve as fluid inlets and the first fluid port 27 may serve as a fluid outlet.

Beneficially, the blood flow assist system 1 can be delivered percutaneously to a treatment location in the patient. FIG. 1D shows the pump 2 disposed within an elongate sheath 28. As shown, the struts 19 are held in a collapsed configuration by the inner wall of the sheath 28. In the collapsed configuration, the struts 19 can be compressed to a diameter or major lateral dimension at one or more locations that is approximately the same (or slightly smaller than) the diameter of the shroud 16. The patient can be prepared for the procedure in a catheterization lab in a standard fashion, and the femoral artery can be exposed. The sheath 28 (or a dilator structure within the sheath 28) can be passed over a guidewire and placed into the treatment location, for example, in the descending aorta. After the sheath 28 is placed, the pump 2 can be advanced into the sheath 28, with the pump 2 disposed in the mid-thoracic aorta, approximately 4 cm below the take-off of the left subclavian artery. In other embodiments, the pump 2 and sheath 28 can be advanced together to the treatment location. Positioning the pump 2 at this location can beneficially enable sufficient cardiac support as well as increased perfusion of other organs such as the kidneys. Once at the treatment location, relative motion can be provided between the sheath 28 and the pump head (e.g., the sheath 28 can be retracted relative to the pump 2, or the pump 2 can be advanced out of the sheath 28). The struts 19 of the localization system can self-expand radially outwardly along the radial axis R due to stored strain energy into the deployed and expanded configuration shown in FIGS. 1A-1C. The convex contact pads 24 can engage the blood vessel wall to stabilize (e.g., anchor) the pump 2 in the patient's vascular system. Once anchored at the treatment location, the clinician can engage the control system to activate the motor 30 to rotate the impeller assembly 4 to pump blood.

Thus, in some embodiments, the pump 2 can be inserted into the femoral artery and advanced to the desired treatment location in the descending aorta. In such arrangements, the pump 2 can be positioned such that the distal end 22 is upstream of the impeller 6, e.g., such that the distally-located first fluid port 27 is upstream of the second fluid port(s) 25. In embodiments that access the treatment location via the femoral artery, the first fluid port 27 can serve as the inlet to the pump 2, and the second ports 25 can serve as the outlet(s) of the pump 2. In other embodiments, however, the pump 2 can be inserted percutaneously through the left subclavian artery and advanced to the desired treatment location in the descending aorta. In such arrangements, the pump 2 can be positioned such that the distal end 22 of the system 1 is downstream of the impeller 6, e.g., such that the distally-located first fluid port 27 is downstream of the second fluid port(s) 25. In embodiments that access the treatment location through the left subclavian artery, the second fluid port(s) 25 can serve as the inlet(s) to the pump 2, and the first port 27 can serve as the outlet of the pump 2.

When the treatment procedure is complete, the pump 2 can be removed from the patient. Relative motion opposite to that used for deploying the pump 2 can be provided between the sheath 28 and the pump 2 (e.g., between the sheath 28 and the impeller assembly 4 and pump housing 35) to collapse the struts 19 into the sheath 28 in the collapsed configuration. In some embodiments, the pump 2 can be withdrawn from the sheath 28 with the sheath 28 in the patient's body, and the sheath 28 can subsequently removed. In other embodiments, the sheath 28 and the pump 2 can be removed together from the patient's body.

II. Modified Sleeve Bearings

As explained above, in some embodiments the sleeve bearing 15 can support a distal end portion 5A of the impeller shaft 5, which can support the first impeller 6 and can also serve as a flow tube. Designs may be generally described from a perspective in which the central axis of rotation of the impeller assembly 4 is oriented along the longitudinal axis L of the system 1, e.g., vertically for purposes of discussion in some instances. As used herein, proximal and distal ends (or end portions) of a component may be axially spaced apart along the longitudinal axis L of the system 1. Thus, the sleeve bearing 15 may be described interchangeably in terms of an associated length or height, which extend along the longitudinal axis L. Generally, a rotating member (a shaft or tube such as the impeller shaft 5 shown and described herein) rotating inside a tubular sleeve or bearing has a bearing surface that is cylindrically shaped as an open right circular cylinder. This standard bearing design has circular proximal and distal edges (e.g., upper and lower interface edges) that are perpendicular to the longitudinal axis L of the rotating member or axis of rotation, and a cylindrical bearing surface between the edges that remains covered and unexposed by the bearing body. Further, there is a circular set of points where the rotating member (e.g., the shaft 5) and bearing interface with one another, which may be referred to herein as a bearing interface or interface edge. In other words, any point on this circle on the rotating member is always perpendicularly aligned with the edge of the sleeve. This condition has been shown to encourage thrombus formation at the sleeve edge(s). This thrombus may grow to form a complete ring around the sleeve edge, thereby impeding proper operation.

The designs of the modified sleeve bearing 15 described herein have a novel design to reduce or prevent thrombus formation during operation. Turning to FIGS. 2A-2E, one embodiment of such a sleeve bearing 15 is illustrated. The sleeve bearing 15 can comprise an inner support structure including an inner sleeve 37 that supports the distal portion 5A of the impeller shaft 5. The inner sleeve 37 can be mechanically coupled to the first impeller 6 in some embodiments, e.g., by way of a thrust ring bearing 14 (see FIG. 6). The thrust bearing 14 can be laser welded to the inner sleeve 37 in one embodiment. In other embodiments, there may be no thrust bearing 14 between the first impeller 6 and the inner sleeve 37. The sleeve bearing 15 can further include an outer support structure comprising an outer annular or cylindrical member, sometimes referred to herein as an outer sleeve or outer bearing carrier 38 connected to the shroud 16. The outer sleeve or bearing carrier 38 can comprise a small radially outer portion of the sleeve bearing 15. A connecting structure 39 can extend radially between the inner sleeve 37 and the outer bearing carrier 38 to connect the inner sleeve 37 and the outer bearing carrier 38. In variations the connecting structure 39 can be coupled directly to the shroud 16. The outer bearing carrier 38 can be eliminated in one embodiment. The outer bearing carrier 38 can be integrated into or be part of the shroud 16, such that the structure is a monolithic construction and not the assembly of multiple parts. In other variations the connecting structure 39 can be indirectly coupled to the shroud 16 through a structure other than the annular member or bearing carrier 38.

As explained herein, the pump 2 can have a primary or first flow pathway 3A. Blood can flow along the first flow pathway 3A between the outer bearing carrier 38 and the inner sleeve 37 and along an exterior surface of the first impeller 6. A majority of the blood flow (e.g., a majority of the momentum of the total blood flow) through the pump 2 can pass along the primary or first flow pathway 3A. The first flow pathway 3A can extend radially between the rotating first impeller 6 and the stationary pump housing 35. Accordingly, blood can flow over the rotating outermost surface of the first impeller 6 between the first impeller 6 and the stationary inner wall of the pump housing 35. The pump 2 can also have a secondary or second flow pathway 3B along a lumen of the impeller shaft 5, which as explained herein can serve as a flow tube. A minority of the total blood flow can flow along the secondary flow pathway 3B. For example, in some embodiments, the volume flow of blood along the secondary flow pathway 3B can be in a range of 0.5% to 10% of the volume flow of blood along the primary flow pathway 3A, in a range of 1% to 5% of the volume flow of blood along the primary flow pathway 3A, or in a range of 2% to 3% of the volume flow of blood along the primary flow pathway 3A.

Figure 2A:
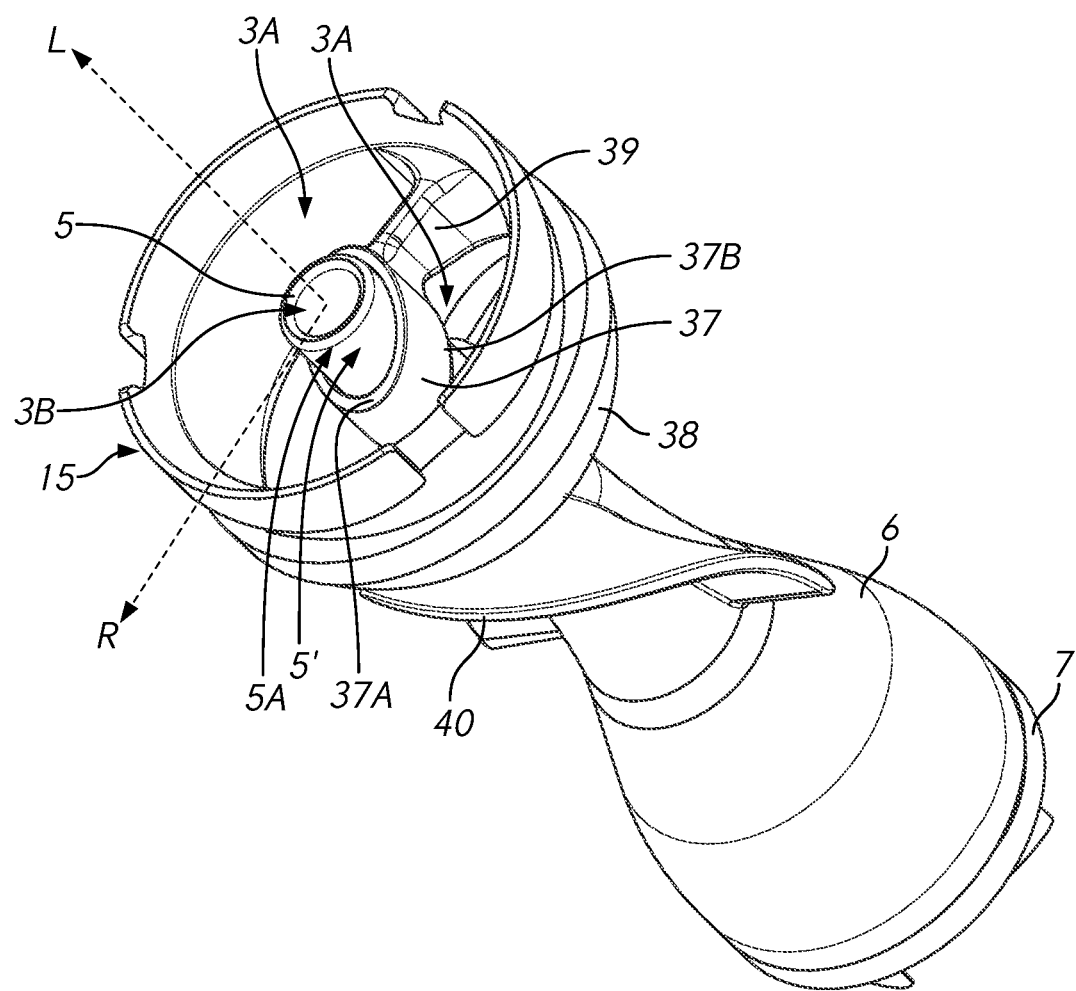
FIG. 2A is a schematic perspective view of a modified sleeve bearing disposed about an impeller shaft distal an impeller of an impeller assembly.
Figure 2B:
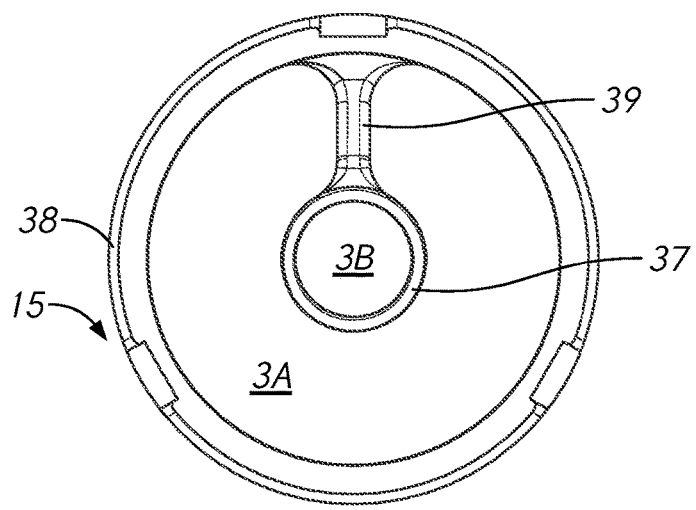
FIG. 2B is a schematic front plan view of the sleeve bearing of FIG. 2A.
Figure 2C:
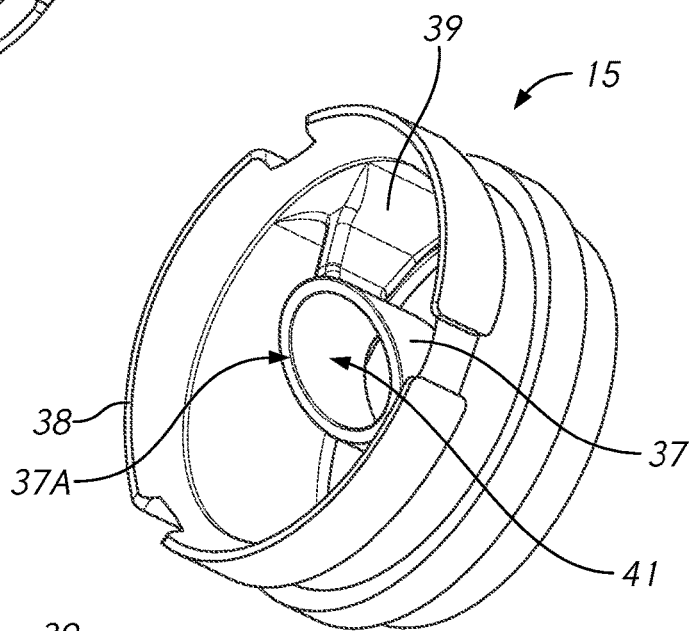
FIG. 2C is a schematic side perspective view of the sleeve bearing of FIG. 2B.
Figure 2D:
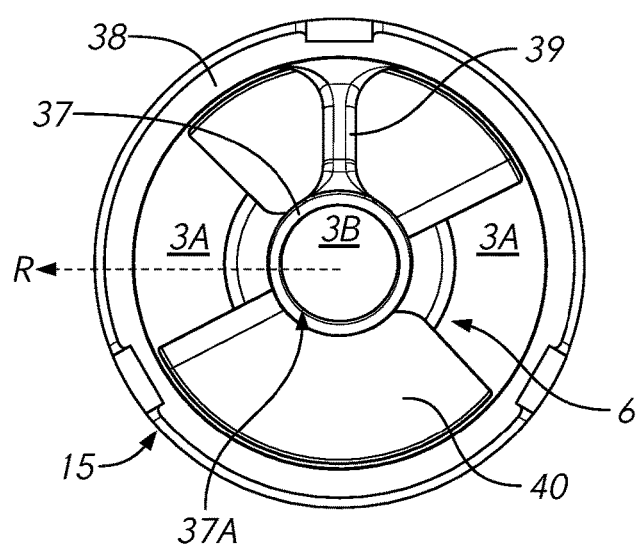
FIG. 2D is a schematic front plan view of the sleeve bearing and impeller assembly of FIG. 2A.
Figure 2E:
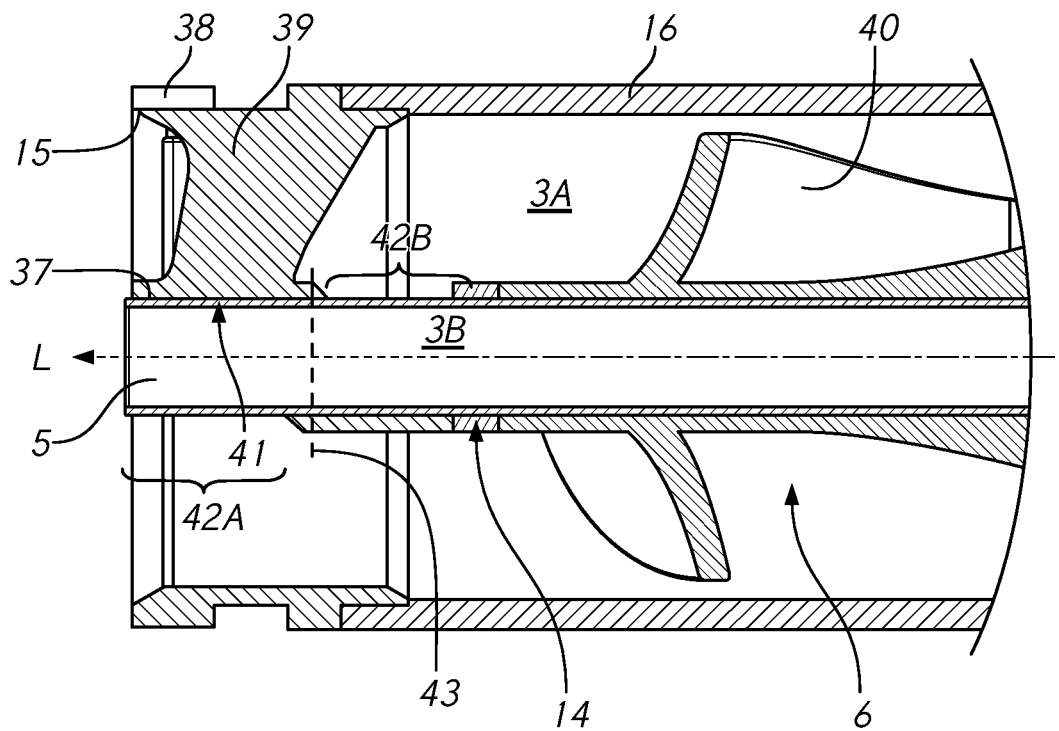
FIG. 2E is a schematic side sectional view of the impeller assembly and sleeve bearing of FIG. 2D.

As shown in FIGS. 2A, 2C, and 2E, the inner sleeve 37 can have a bearing interface surface 41 extending between a proximal edge 37B (or "lower edge" if viewed vertically) and a distal edge 37A (or "upper edge" if viewed vertically) spaced apart from the proximal edge 37B along the longitudinal axis L. The sleeve bearing 15 can be shaped so that one or more bearing interface surfaces 41 and/or interface edges (37A, 37B) of the inner sleeve 37 are not perpendicular to the axis of rotation or longitudinal axis L of the sleeve bearing 15. In one embodiment, the bearing interface surface 41 may comprises edges 37A, 37B that form ellipse(s) tilted or tapered with respect to the longitudinal axis L of the sleeve bearing 15 (FIGS. 2A-2E). In another embodiment, as explained below, the bearing surface(s) 41 may vary in a sinusoidal way to create crenulated edge(s) (see FIG. 2F). These or other shapes that result in non-circular sleeve edges 37A, 37B ensure that there are no points on the rotating member or impeller shaft 5 that remain aligned with the sleeve edges 37A, 37B throughout the rotation of the rotating member (e.g., shaft 5), thereby minimizing the potential for thrombus formation. Whereas conventional designs leave an entire right circular cylinder section covered, the modified sleeve bearings 15 expose at least one point on the rotating member or shaft 5 throughout the entire length (or height if the sleeve bearing is viewed as being vertically oriented) of the sleeve bearing 15 so that the rotating member bearing interface surface 41 is only covered by the sleeve bearing for a portion of rotation. As such, the interfacing bearing surface(s) 41 may have better exchange of the lubricating layer of blood than conventional designs.

Thus, in some embodiments, the distal edge 37A can comprise a distal boundary of the inner sleeve 37. The distal boundary (e.g., the distal edge 37A) can be angled relative to the axis of rotation (which is aligned with the longitudinal axis L) such that, in a cross-section taken perpendicular to the axis of rotation L, only a portion of the distal boundary (e.g., distal edge 37A) is disposed about the impeller shaft 5 at a selected axial location along the axis of rotation. In some embodiments, only a portion of a proximal boundary can be disposed about the impeller shaft 5 at a selected axial location along the axis of rotation. For example, as shown in FIG. 2E, the bearing interface surface 41 can have exposed axial regions 42A, 42B comprising axial location(s) at which an exterior surface 5' (see FIG. 2A) of the impeller shaft 5 is cyclically exposed to blood that flows along the first flow pathway 3A. In the exposed axial regions 42A, 42B, the bearing interface surface 41 is disposed about only a portion of a perimeter (e.g., circumference) of the impeller shaft 5. Accordingly, when the impeller shaft 5 is rotated about the axis of rotation (aligned with the longitudinal axis L), an exterior surface of the impeller shaft 5 at a selected axial location within the exposed axial regions 42A, 42B is cyclically exposed to blood flow in the first pathway 3A during operation of the blood flow assist system 1.

In some embodiments, such as that shown in FIGS. 2A-2E, the inner sleeve 37 may be partially axially overlapping along the longitudinal axis L. As shown in FIG. 2E, for example, at an example overlapping cross-sectional plane 43, the bearing surface 41 of the inner sleeve 37 may be disposed completely around the exterior surface of the impeller shaft 5 such that the exterior surface 5' of the shaft 5 at that overlapping cross-sectional plane 43 is not exposed to blood flow in the first pathway 3A. For example, in some embodiments, the sleeve bearing 15 can have a length along the longitudinal axis L. The inner sleeve 37 may be partially overlapping by an amount in a range of 1% to 50% of the length of the sleeve bearing 15, in a range of 5% to 50% of the length of the sleeve bearing 15, in a range of 10% to 50% of the length of the sleeve bearing 15, in a range of 20% to 40% of the length of the sleeve bearing 15, or in a range of 25% to 35% of the length of the sleeve bearing 15 (e.g., about 30% of the length of the sleeve bearing 15 in some embodiments).

Figure 2F:
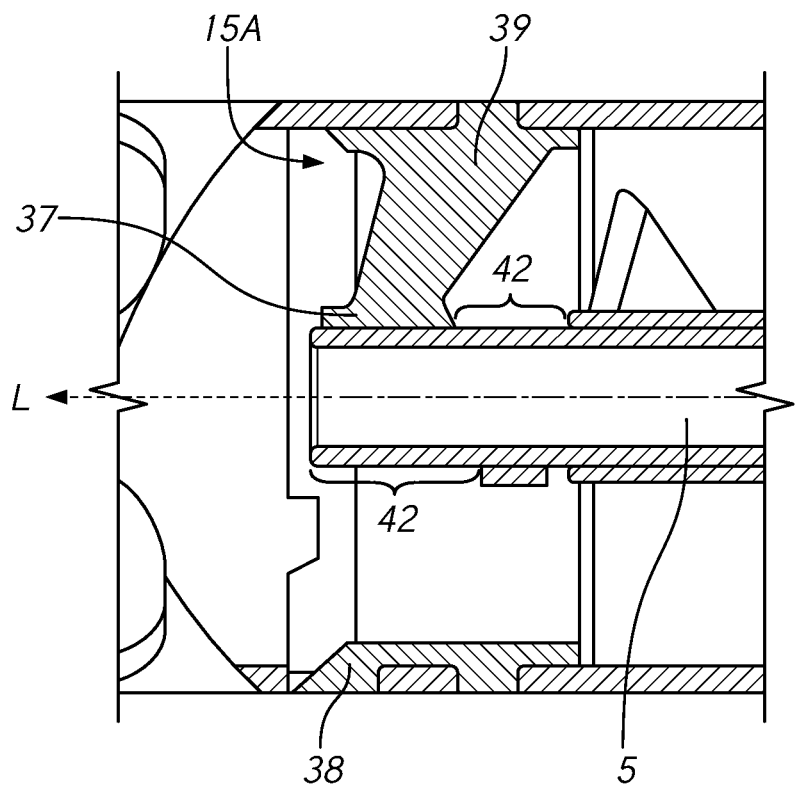
FIG. 2F is a schematic side sectional view of a non-overlapping sleeve assembly, according to another embodiment.

In other embodiments, such as that shown in FIG. 2F, a sleeve bearing 15A can comprise an inner sleeve 37 which may be non-overlapping such that there are no points on the exterior surface 5' of the impeller shaft 5 that remain covered by the bearing interface surface 41 during rotation of the impeller shaft 37. In FIG. 2F, all axial locations along the length of the inner sleeve 37 comprise an exposed axial region 42, such that the bearing surface 41 of the inner sleeve 37 is disposed only partially about the perimeter of the impeller shaft 5 at all axial locations along the length of the inner sleeve 37. For example, the edge(s) 37A, 37B can comprise non-circular edge(s) that ensures that there are no points on the rotating member or shaft 5 that remain aligned with the sleeve edge(s) 37A, 37B throughout an entire rotation of the rotating member or shaft 5. The sleeve bearing 15A can therefore expose at least one point on the rotating member or shaft 5 throughout an entire length (or height) of the sleeve bearing 15A so that the exterior surface 5' of the shaft 5 is only covered by the inner sleeve 37 for a portion of rotation.

Accordingly, in some embodiments the bearing edges 37A, 37B are shaped so that maximum length (or height) of the lower or proximal edge 37B is above minimum length (or height) of the upper or distal edge 37A in one or more locations around the circumference of the inner sleeve 37 (FIGS. 2E & 3F). In these embodiments, there is at least one point on the bearing interface surface 41 throughout the length (or height) of the bearing interface surface 41 that is exposed and that is not covered by the inner sleeve 37 of the sleeve bearing 15, 15A. In other words, the sleeve bearing 15, 15A never covers 360° of the rotating member or shaft 5 throughout the entire length or height of the bearing interface region 41. This interrupted contact of the disclosed embodiments promotes exchange of a lubricating layer blood over the entire bearing interface 41 and does not allow blood to stagnate or become trapped.

In some embodiments, the tilt or taper of the sleeve edges 37A, 37B with respect to the longitudinal axis L (and the axis of rotation) may also generate or enhance fluid dynamic forces that contribute to proper bearing operation and reduce contact and wear of the bearing parts. As one non-limiting example, the fluid near the surface of a particular spot on the rotating member (e.g., shaft 5) may experience increases and decreases in pressure as it moves under and out from under the inner sleeve 37. These pressure changes contribute to lubricating layer formation and dispersal.

The interface between the sleeve bearing 15, 15A and the rotating member (e.g., shaft 5) is lubricated by blood. Depending on geometry, materials used, and operating conditions, this lubrication may be hydrodynamic lubrication, elastohydrodynamic lubrication, boundary lubrication, or mixed lubrication. The varying exposure of the rotating member surface and/or varying edge profile of the sleeve bearing edges 37A, 37B may be designed to help encourage a fluid wedge to improve lubrication. As a non-limiting example, viscous drag from a surface patch of the rotating member or shaft 5 may increase fluid pressure above that surface patch as it rotates under the sleeve edge(s) 37A, 37B. In some embodiments, the cross-section of the inner bearing surface 41 of the sleeve 37 may optionally be made non-circular to aid in wedge pressure generation, for example by varying the wall thickness of the inner sleeve 37. The sleeve edge profile of the edges 37A, 37B may be beveled or rounded to augment this pressure generation.

Figure 2G:
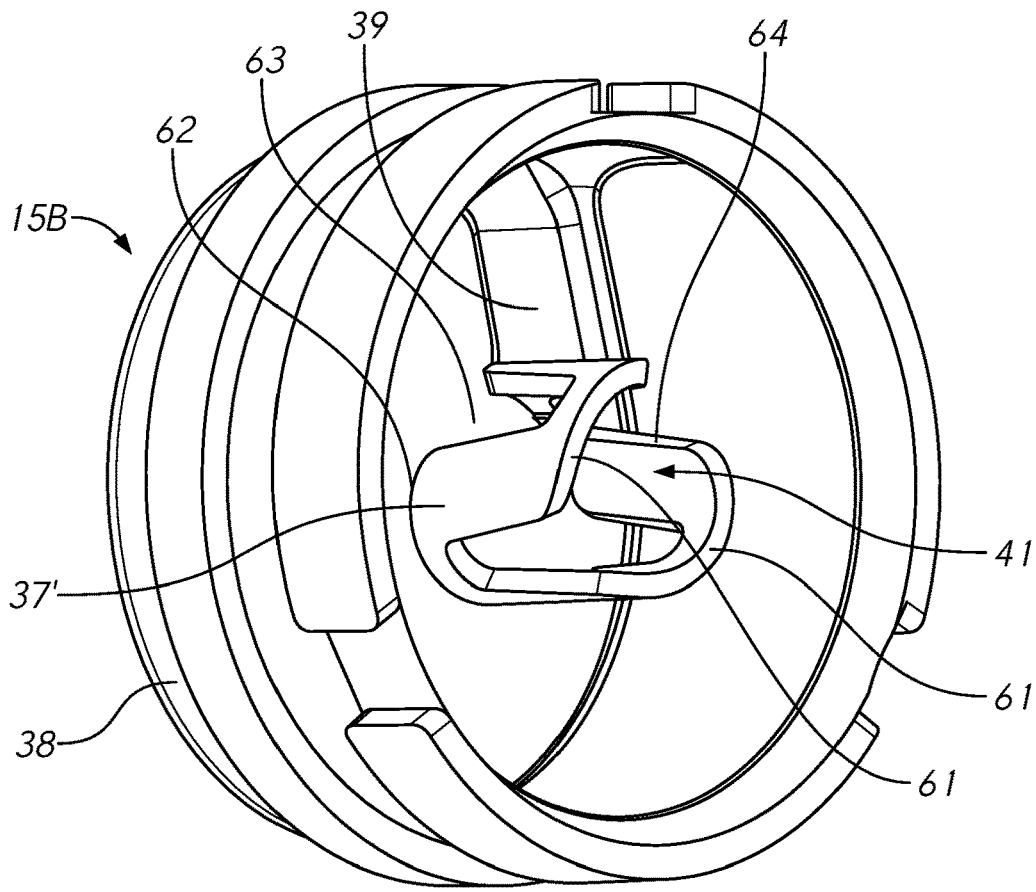
FIG. 2G is a schematic perspective view of a sleeve bearing having a crenulated pattern.
Figure 2H:
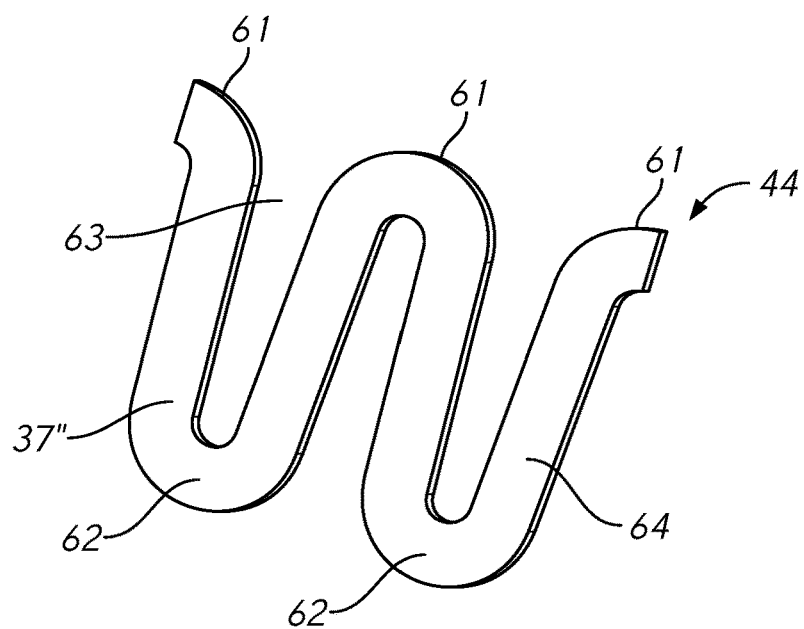
FIG. 2H is a schematic plan view of a sinusoidal pattern of the sleeve bearing of FIG. 2G.

FIGS. 2G and 2H illustrate another example of a sleeve bearing 15B that has a non-overlapping design. The sleeve bearing 15B comprises a crenulated bearing in which the bearing interface surface 41 is disposed about the longitudinal axis L in a repeating, undulating or in some cases a sinusoidal pattern 44. The sinusoidal pattern 44 can have alternately exposed gaps about the perimeter of the impeller shaft 5 during rotation such that all axial locations along the length of the sleeve bearing 15B are cyclically exposed to blood flow during operation of the system 1. FIG. 2G shows the inner sleeve 37' can have an undulating pattern that has a plurality of (e.g., two) distal peaks 61 and a plurality of (e.g., two) proximal peaks 62. For example, as shown in FIG. 2G, the peaks 61, 62 can be generally flat with arcuate sections 64 extending between the peaks 61, 62. A gap 63 between the arcuate sections 64 can provide for the cyclical exposure of the shaft 5 to blood flow. Thus, during rotation, the shaft 5 can transition from covered by the arcuate sections 64 to being uncovered and exposed through the gaps 63. In other variations, there can be more than two peaks in the undulating pattern of the sleeve 37'. FIG. 2H shows an inner sleeve 37" with another crenulated structure with a sinusoidal patterns, e.g., with curved peaks 61, 62. In some arrangements, the use of curved peaks 61, 61 (as opposed to sharp or flat peaks) may beneficially allow for smoother flow profiles.

The rotating member 5 and the sleeve bearings 15, 15A, 15B may each be made of any suitable blood compatible material. As a non-limiting example, the rotating member (e.g., the impeller shaft 5) may comprise a flow tube made out a biocompatible polymer, e.g., of PEEK or polyethylene and/or the sleeve bearing 15, 15A, 15B may be made out of a metal, e.g., titanium or stainless steel. Making the rotating member or shaft 5 as a plastic tube may increase the range over which elastohydrodynamic lubrication is present. For example, the use of materials that enable elastic deformation of the materials during operation can provide an improved pressure profile.

III. Modified Cone Bearings

Figure 6:
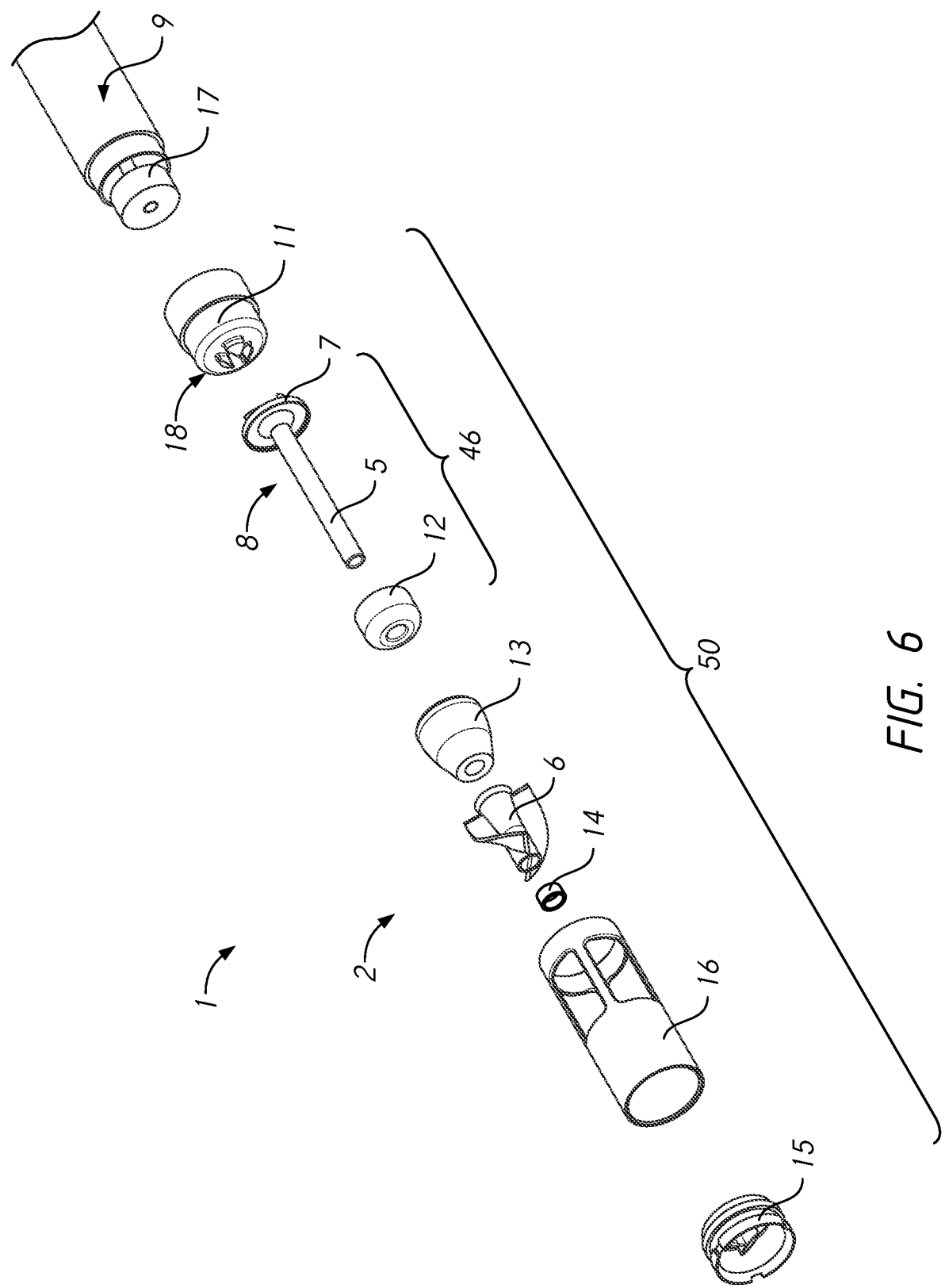
FIG. 6 is a schematic, perspective exploded view of a blood flow assist system according to various embodiments.

As shown in FIGS. 1A, 1C and 6, the drive unit 9 can comprise a drive magnet 17 and a drive bearing 18 between the drive magnet 17 and the impeller assembly 4. The drive bearing 18 can provide a magnetic coupling and a fluid bearing interface between the drive magnet 17 and a rotor assembly 46 that comprises the driven or rotor magnet 12 and an integrated rotor core 8 that includes the impeller shaft 5 and a secondary impeller 7, as shown in FIG. 6. In various embodiments, the drive bearing 18 can comprise a segmented cone bearing. Cone bearings can comprise a convex (e.g., generally conical) shaped member 45 seated inside a generally concave (e.g., conical) opening 32 or cavity of the rotor assembly 46. The concave opening 32 can serve as a concave bearing surface sized and shaped to mate with the convex member 45. The concave opening 32 can comprise an angled concave cavity sized to receive the convex member 45. The drive unit 9 can comprise a convex member sized to fit within the angled cavity of the concave opening 32.

The bearing interface region of this bearing design can be formed by the matching surfaces of the conical or convex member 45 and the conical or concave opening 32 and the space between them. A cone bearing can provide both axial and radial confinement. The axial confinement from a single cone bearing can be in one direction only. Cone bearings with steep slopes provide relatively more radial confinement, and cone bearings with shallower slopes provide relatively more axial confinement. In some embodiments, the conical shaped member 45 can be modified to reduce hemolysis and/or clotting. In some embodiments, the conical member 45 can be truncated by a cylinder coaxial to the axis of the cone (or axis of rotation) to remove base portions of the cone. In some embodiments, the conical member 45 can be truncated by a plane perpendicular to the axis of the cone (creating a frustrum or a frustoconical surface). In other embodiments, the conical member 45 can be truncated by both a cylinder and a cone. In some embodiments, the surface of the conical opening 32 may be modified in a similar manner in conjunction with the conical member 45 or instead of the conical member 45. One or the other or both of the surfaces of the conical member 45 and conical opening 32 may also be modified by holes, gaps, channels, grooves, bumps, ridges, and/or projections. Each of the surfaces of the conical member 45 and conical opening 32 may also be formed as part of other components of the pump with any overall shape.

Given the general possibility of holes, grooves, channels, or gaps in either the conical member 45 and/or conical opening 32, either of their surfaces comprise of a plurality of separate bearing surfaces in the plane of the generally conical shape defining the member 45 or opening 32. In such a manner the opening 32 and/or the conical member 45 of the bearing pair may be formed by a plurality of separate surfaces or a segmented surface. The plurality of separate surfaces or the segmented surface that make up either the conical member 45 or conical opening 32 of the bearing pair may extend from the same component or part, or may extend from distinct components or parts. Grooves and gaps in either the conical member 45 and/or conical opening 32 may be created by removing material from a single generally conical surface or by using a plurality of separate surfaces.

In some embodiments of a modified cone bearing, the conical member 45 of the bearing pair can comprise a convex bearing surface having a segmented frustoconical shape formed from a plurality of distally-extending segments 33 (FIGS. 3A-3D). The distally-extending segments 33 can extend distally from the drive unit cover 11. The segments 33 can be spaced apart circumferentially to define at least one channel 34 between adjacent segments 33. Three segments 33 are shown in FIGS. 3A-3D, but any suitable number of segments 33 may be utilized. As shown, the segments 33 can be separate components arising from a common part with gaps or channels 34 between them, but the segments 33 may also be separated by shallow or deep grooves. The gaps, grooves or channels 34 may follow any path. In the illustrated embodiment, the channel(s) 34 extend radially outward from a central recess or hollow 31 (also referred to herein as a void) at a location proximal a proximal end portion 5B of the impeller shaft 5. In some embodiments, the width and depth of any groove or channel 34 may vary along its path. In some embodiments, two or more channels 34 may join or separate. In certain embodiments, two or more channels 34 may join to form the central hollow area 31 coaxial with the axis of the conical surfaces and/or with the longitudinal axis of rotation L. In some embodiments, the conical opening 32 of the bearing pair can be a continuous (e.g., no gaps, channels, or grooves), generally conical surface. The relative angles of the cone bearings (e.g., the segments 33) and spacing between segments 33 can be selected to provide a desired flow profile through the channel(s) 34 described herein. For example, increased spacing between the segments 33 can provide increased flow through the channels 34. Together, the segmented conical member 45 of the drive bearing 18 with channels 34 between the segments 33 and the continuous conical opening 32 can serve as a "segmented cone bearing".

The channels 34 between the segments 33 allow interrupted contact between bearing surfaces similar to the interrupted contact described above for the modified sleeve bearing 15, 15A, 15B discussed previously. This interrupted contact provides, without limitation, benefits for the segmented cone bearing analogous to those it provides to the modified sleeve bearing 15, 15A, 15B. For example, in embodiments in which the conical opening 32 is part of the rotating member (e.g., the impeller shaft 5), the channels 34 between the segments 33 can ensure that at least one point throughout the length or height of the conical opening 32 on the rotating member 5 is intermittently exposed by the conical opening 32 and not continuously covered by the bearing pair. This design promotes exchange of a lubricating layer blood over the entire bearing interface. The channels 34 also generate pressure changes that contribute to lubricating layer formation and dispersal as described above for the sleeve bearing 15, 15A, 15B.

In some embodiments, additional features may promote blood flow through the central hollow 31 and channels 34 of the segmented cone bearing. In some embodiments blood may flow in through the channels 34 and exit via the central hollow 31. In other embodiments blood may flow into the central hollow 31 (e.g., from the secondary flow pathway 3B of the impeller shaft 5) and exit via the channels 34. This net flow of blood through the central hollow 31 and channels 34 may serve to ensure the volume of blood in the channels 34 and central hollow 31 is constantly flowing to provide a source of fresh blood for lubricating layer exchange, to carry away heat, and/or to reduce the time that blood is exposed to conditions within the bearing region that may increase the potential for hemolysis or thrombus formation. Accordingly, in various embodiments, a concave bearing surface (which can comprise or be defined by the concave opening 32) can include a fluid port to deliver blood proximally along the second flow pathway 3B. The convex bearing surface (which can comprise the convex member 45) can including a void (e.g., the central hollow 31), which can be disposed on the longitudinal axis L. The one or more channels 34 can extend radially outward from the void or central hollow 31. The void can be in fluid communication with the fluid port (e.g., an interface between the flow tube 5 and the conical opening 32) so as to direct blood radially outward along at least one channel 34.

Figure 4B:
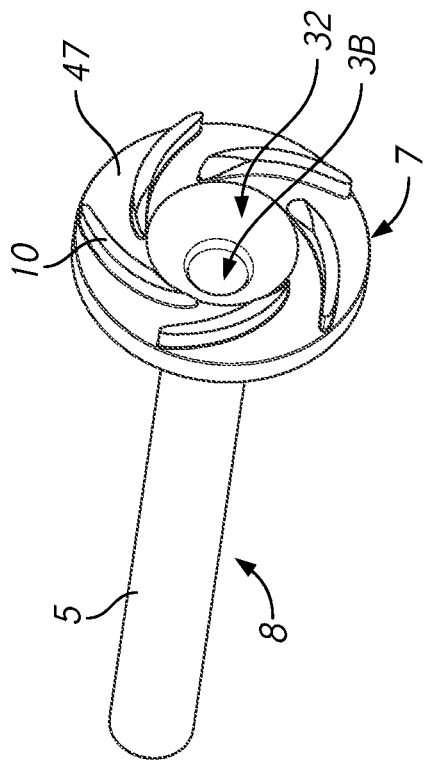
FIG. 4B is a schematic perspective view of a proximal portion of the integrated rotor core of FIG. 4A.
Figure 4D:
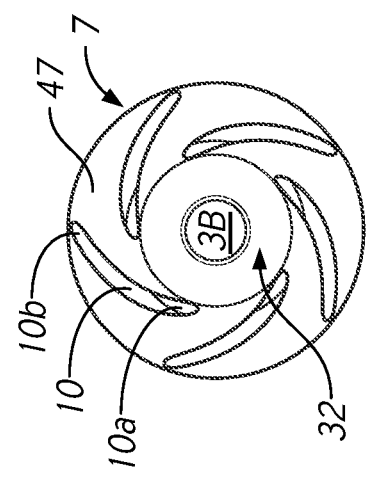
FIG. 4D is a schematic proximal end view of the integrated rotor core of FIG. 4C.
Figure 4A:
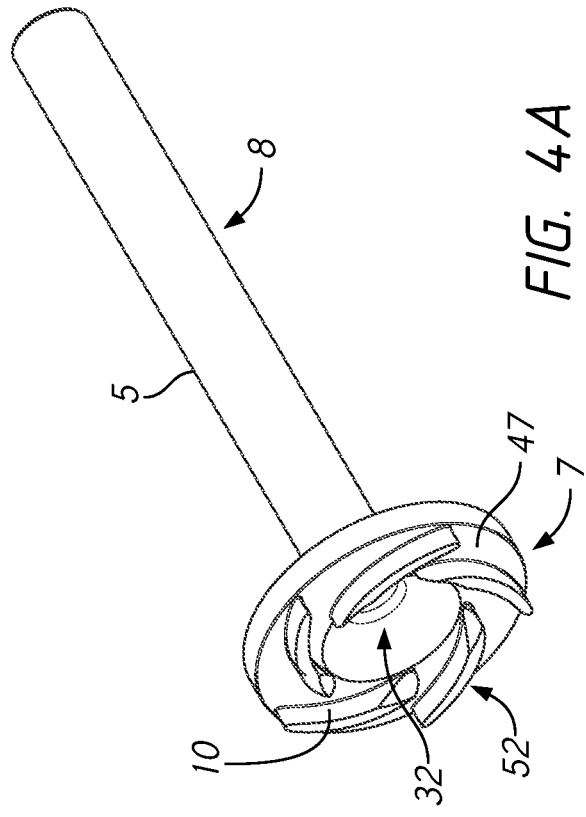
FIG. 4A is a schematic perspective view of an integrated rotor core comprising an impeller shaft with flow tube and a secondary impeller.
Figure 4C:
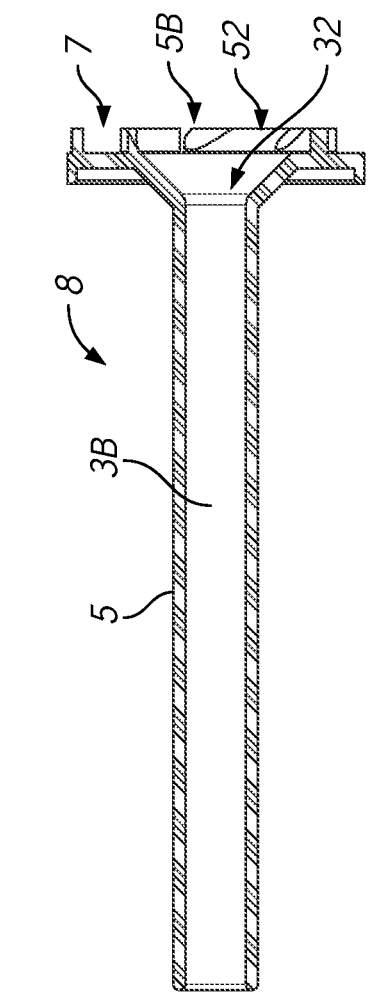
FIG. 4C is a sectional view taken along the longitudinal axis of the rotor core of FIG. 4B.
Figure 5A:
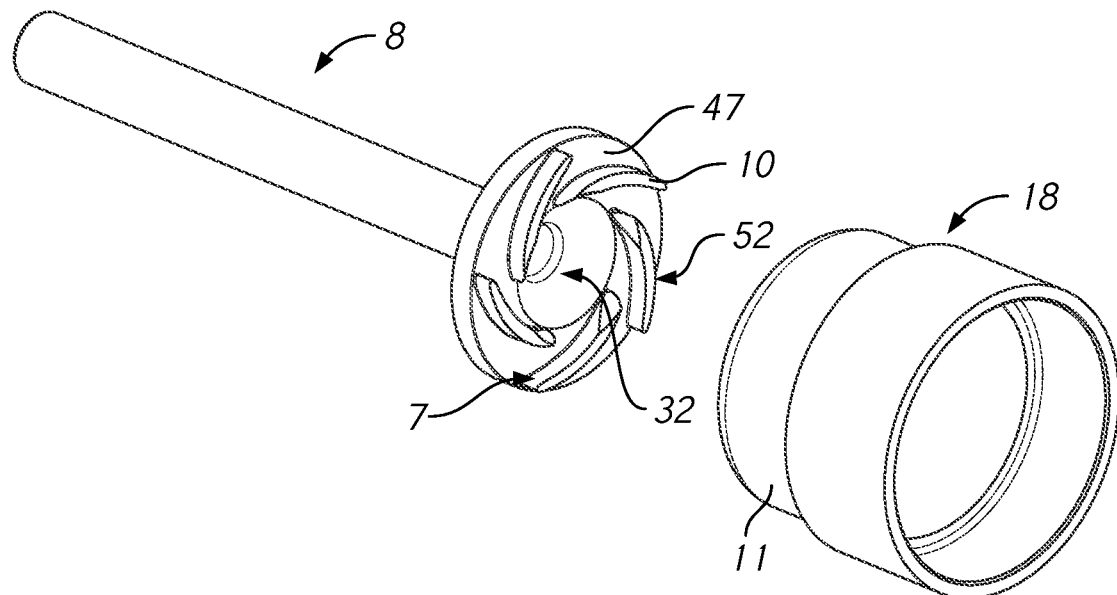
FIG. 5A is a schematic perspective, exploded view of a segmented cone bearing comprising a proximal portion of the integrated rotor core and the drive bearing.
Figure 5B:
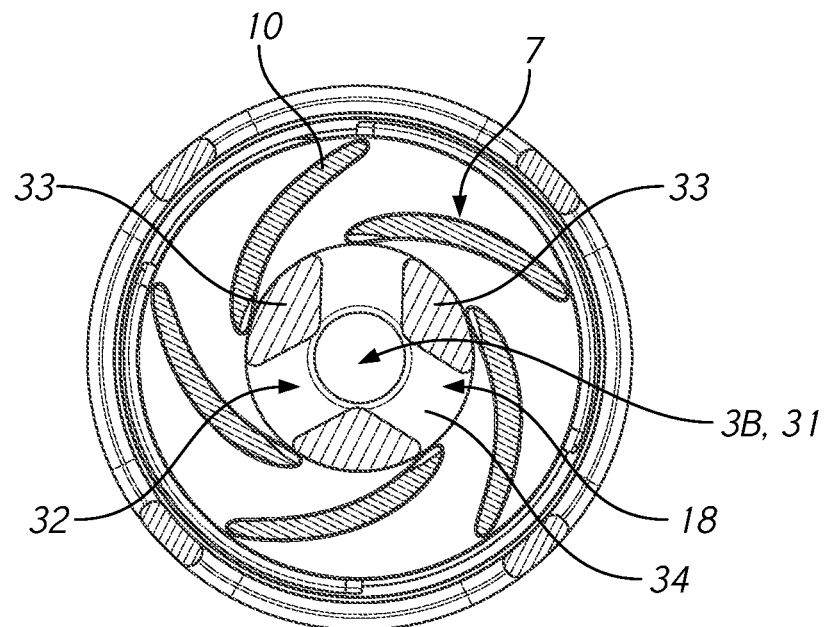
FIG. 5B is a distal end sectional view of the secondary impeller and drive bearing.

As shown in FIG. 5A, the segments 33 of the convex member 45 can be shaped to fit within the concave bearing surface comprising the concave opening 32. In some embodiments, as shown in FIGS. 4A-5B, a direct secondary flow pathway 3B (for example through the flow tube of the impeller shaft 5 shown in FIGS. 4B-4D and 5B) may provide proximally-flowing blood into the central hollow 31. In some embodiments a secondary or second impeller 7 may be used to drive the secondary flow of blood through the bearing region, e.g., through the second flow pathway 3B, the central hollow 32, and radially outwardly through the channel(s) 34. The primary impeller 6 of the pump and/or the additional secondary impeller 7 may assist in drawing the blood proximally and directing the blood radially outwardly along the channel(s) 34. FIGS. 4A-4D show the secondary impeller 7 that draws blood out through the channels 34 of the segmented cone bearing. As explained herein, the secondary impeller 7 and impeller shaft 5 can form an integrated rotor core 8. The secondary impeller 7 can have a plurality of vanes 10 as explained herein to assist in directing blood radially outward through the channel(s) 34 of the drive bearing 18.

Keeping the segmented cone bearing elements or segments 33 near the central longitudinal axis L of the pump can have several advantages. For example, in the illustrated embodiment, the bearing elements 33 can be more directly exposed to the blood flow from the flow tube of the impeller shaft 5 along the second flow pathway 3B. Further, the bearing elements 33 can have a smaller radius where the linear speed of the rotating member is lower. Placing the bearing elements or segments 33 near the axis L of the pump allows the vanes 10 of the secondary impeller 7 to be placed at a greater radius where the linear speed of the rotating member or shaft 5 is higher.

FIG. 3D shows an embodiment in which the channels 34 between the segments 33 follow a curved path from the central hollow 31. The channels 34 can be configured to increase flow and reduce shear forces on the blood. In some embodiments, the depth of the channels 34 may be varied to form a central flow diverter 31a as shown in, e.g., FIG. 3E. The flow diverter 31a may comprise a distally-extending projection (e.g., a cylindrical projection, a conical projection, a pyramidal projection, etc.) disposed in a central region of the bearing between the segments 33. In the illustrated embodiment, the flow diverter 31a can comprise a symmetrical flow diverter. The flow diverter 31a may aid blood coming from the flow tube or lumen of the shaft 5 to transition from axial flow to radial flow to exit through the channels 34. The flow diverter may optionally be manufactured as one or more separate pieces that are then attached in the central hollow 31 and/or channels 34. In some embodiments, the flow diverter 31a may comprise a generally right cylindrical shape extending distally from the bearing 18. In other embodiments, the flow diverter 31a can have a tapered, for example, conical, profile.

The interface between the segments 33 of the conical member 45 and concave, e.g., conical, opening 32 of the segmented cone bearing can be lubricated by blood. Depending on geometry, materials used, and operating conditions, this lubrication may be hydrodynamic lubrication, elastohydrodynamic lubrication, boundary lubrication, or mixed lubrication. The channels 34 between the segments 33 of the conical member 45 of the bearing pair may promote fluid exchange so that a portion of the blood that makes up the lubricating layer between a region of the conical opening 32 of the bearing pair over one segment 33 of the conical member of the bearing pair is replaced by fresh blood in the lubricating layer that forms between that same region of the conical opening 32 of the bearing pair and the next segment 33 of the conical member of the bearing pair during rotation. The width and depth of the channels 34 can be altered to encourage this exchange. In various embodiments, the height and lateral spacing of the segments 33 can be selected to provide a desired channel depth and width. For example, a width of the channels 34 can be in a range of 0.02" to 0.06", in a range of 0.03" to 0.05", or in a range of 0.035" to 0.045" (for example, about 0.04" in some embodiments). The surfaces of the segments 33 of conical member of the bearing pair along the channels 34 form the leading and trailing edges (as seen by a region of the conical opening 32 of the bearing pair) of the segments 33 of the conical member of the bearing pair. The distance of the leading and trailing edges from the conical opening 32 may also be modified to encourage fluid exchange. For example, the edges may be beveled or rounded or the distance of the leading and trailing edges may taper away or towards the surface of the conical opening 32.

The surfaces of the segments 33 of the conical member 45 of the bearing pair may also be modified to diverge from a perfect conical surface to promote formation of a lubricating layer. For example, one or more surfaces of the segments 33 of the conical member 45 of the bearing pair may be shaped so the normal distance to the surface of the conical opening 32 of the bearing pair decreases from the leading edge to the trailing edge. Such a surface contour may encourage creation of fluid wedges between the segments 33 of the conical member 45 and the conical opening 32 of the bearing pair for improved lubrication. In another embodiment, the surfaces of the segments 33 of the conical member 45 and conical opening 32 of the bearing pair may be smooth and well matched to allow a relatively thin lubricating layer of relatively uniform thickness to form. It should be appreciated that although conical member 45 and conical opening 32 are described as having a generally conical shape in some embodiments, the member 45 and opening 32 may generally be considered convex member 45 and concave opening 32. The shapes of the convex member and the concave opening 32 may be any suitable mating shapes.

The flow of blood driven by the secondary impeller 7 from the central hollow 31 through the channels 34 provides fresh blood for exchange of the lubricating layers and carries away heat in the bearing region. Both functions are important to reducing the potential for thrombus formation in the segmented cone bearing.

The segments 33 of the conical member 45 of the bearing pair and the conical opening 32 of the bearing pair may each be made of any suitable blood compatible bearing material. As a non-limiting example, the segments 33 of the conical member of the bearing pair may be made out of titanium or stainless steel and/or the conical opening 32 of the bearing pair may be made out of PEEK or polyethylene.

By making one side of the bearing pair relatively hard and the other side of the bearing pair relatively soft, the bearing pair may initially undergo boundary or mixed lubrication where surface asperities are worn to the point where the surfaces of the conical member and conical opening are smooth and well-matched enough for hydrodynamic or elastohydrodynamic lubrication to dominate. Having one side of the bearing pair be relatively softer may increase the range over which elastohydrodynamic lubrication is present. In some embodiments, the continuous, conical opening 32 of the bearing pair will be softer and the segmented, conical member of the bearing pair will be harder. This arrangement may help preserve special geometric features of the segments 33 on the conical member of the bearing pair. In some embodiments, the continuous, conical opening 32 of the bearing pair will be harder and the segmented, conical member 45 of the bearing pair will be softer. This arrangement may help preserve the surface of the opening 32 as a surface of rotation about the longitudinal axis L. In other variations the conical opening 32 and the conical member 45 can be of similar or even the same hardness which can provide the advantage of dimensional and shape stability throughout the operation of the pump 2.

In cases where hydrodynamic lubrication dominates, the normal distance between the segments 33 on the conical member of the bearing pair and the conical opening 32 of the bearing pair may be small enough to exclude red blood cells. In these cases, exchange of the lubricating layer may be less important as long as heat is still transferred away. Given sufficient exclusion of red blood cells, a continuous (e.g., without channels or grooves) conical member 45 of the bearing pair may still demonstrate low potential for thrombus formation as long as heat can be transferred away quickly enough. In some embodiments, this may be accomplished by eliminating or covering the channels 34 to form a continuous conical surface. Blood flow through the covered channels 34 may transfer sufficient heat from the bearing pair.

The segmented bearing embodiments described above provide an additional advantage of enhancing the flexibility of the portion of the pump 2 in the vicinity of the pump head 50. The impeller assembly 4 can be coupled with the drive unit 9 in a manner that permits some motion between the impeller assembly 4 and the cover 11. For example, the pump 2 may be delivered through tortuous or curving vasculature or may be inserted from outside the patient to inside a blood vessel in tight bends. The impeller assembly 4 can tip toward one or more of the segments 33 and away from one or more segments at the conical opening 32 such that proximal end face of the impeller assembly is at a non-parallel angle to the distal face of the cover 11. The motion may be significant compared to a mounting of the impeller assembly 4 on a shaft rotatably supported in a drive unit. The tipping of the impeller assembly 4 can occur with a flexing of the shroud 16, which may be flexed in high bending stress maneuvers. In some embodiments, the shroud 16 is made of an elastic material, such as nitinol, such that the pump head 50 can flex and elastically return to an undeflected state without elongation.

IV. Impeller Shaft with Flow Tube Through Primary Impeller

Figure 9A:
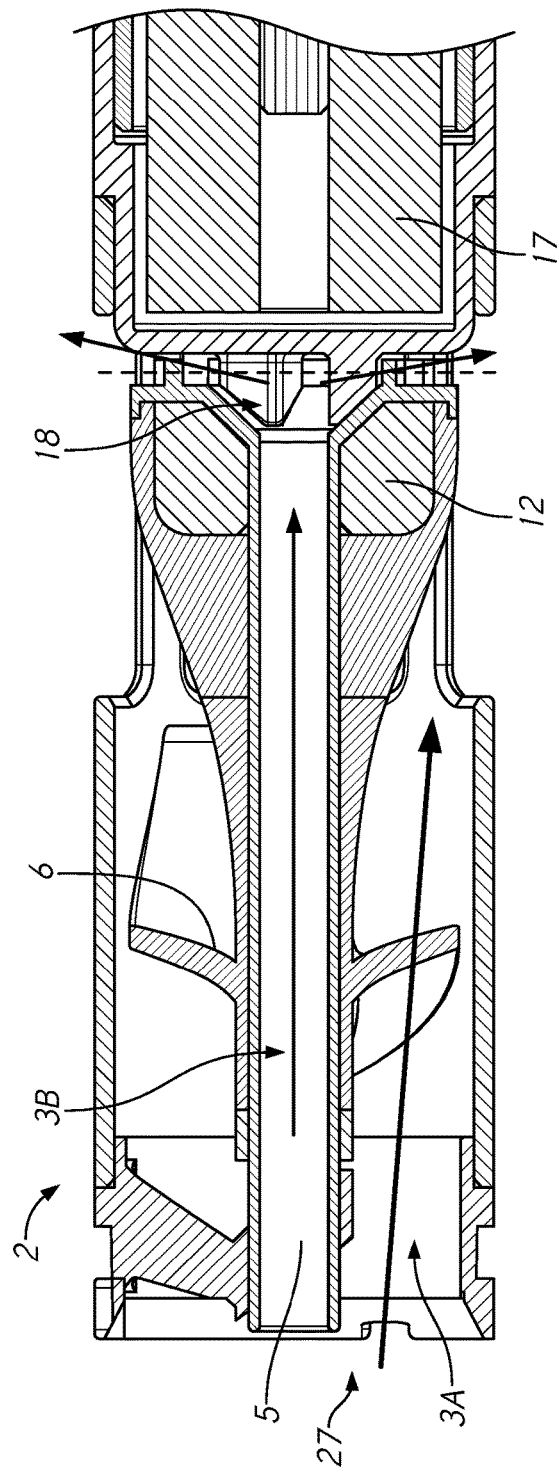
FIGS. 9A and 9B are schematic side sectional views of primary and secondary flow pathways through a pump according to various embodiments.
Figure 9B:
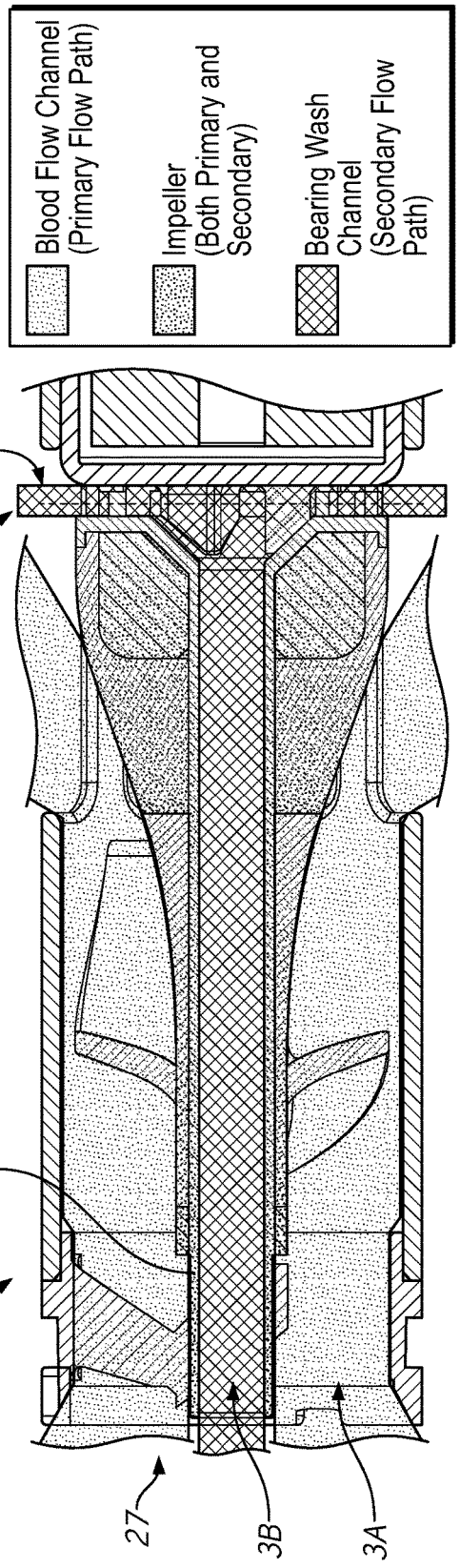

FIGS. 4A-5B and 7 illustrate how the flow tube of the impeller shaft 5 may be routed through the primary impeller 6. This allows for a compact pump rotor assembly 46 in which the primary and secondary flow pathways 3A, 3B are separate and flow in the same direction through the system 1 as shown in FIGS. 9A-9B. Having the two flow paths flow pathways 3A, 3B in the same direction minimizes or reduces the probability of blood recirculating through the pump. In some embodiments, the primary impeller 6 may also have a thrust ring 14 or thrust surface designed to limit axial motion in the upstream or distal direction by contacting a corresponding thrust ring or thrust surface of the sleeve bearing 15. The primary impeller 6 may have the features described in U.S. Pat. Pub. No. 2017/0087288, incorporated by reference herein.

V. Secondary Impeller

As explained herein, the secondary impeller 7 can be disposed proximal the primary impeller 6. In some embodiments, as shown in FIGS. 4A-7, the secondary impeller 7 can comprise a flange 47 extending non-parallel (e.g., radially outward along the radial axis R) from the proximal end portion 5B of the impeller shaft 5 and a plurality of vanes 10 on a proximally-facing surface of the flange 47. The flange 47 can extend non-parallel and radially outward from the impeller shaft 5. In some embodiments, the flange 47 may not extend radially beyond the shroud 16. In some embodiments, the flange 47 may not extend radially beyond an adjacent portion of the impeller assembly 4, e.g., may not extend radially beyond an integrated streamlined fairing 13, discussed below. In some of these embodiments, the flange 47 can comprise a section of the combined rotor surface that lies in a plane perpendicular to the longitudinal axis L. As shown in FIGS. 4A-4C and 5A, the vanes 10 can extend proximally from the flange 47 and can have a curved profile circumferentially about the longitudinal axis L. The vanes 10 can be disposed in the space between the proximal face of the flange 47 and the distal end of the drive unit 9. The concave opening 32 can comprise an angled cavity extending inwardly and distally relative to the generally proximally-facing surface of the flange 47. The rotor magnet 12 can be disposed adjacent a distally-facing surface of the flange 47. Each of the vanes 10 can have an inner end 10a disposed at or near the concave opening 32 and an outer end 10b extending radially and circumferentially outward from the inner end 10a along the flange 47. The flange 47 can be coupled to or formed with the proximal end of the impeller shaft 5. In some embodiments, for example, the flange 47 can be monolithically formed with (e.g., seamlessly formed with) the impeller shaft 5. In other embodiments, the flange 47 and impeller shaft 5 can be separate components that are mechanically connected to one another (e.g., welded or otherwise coupled). In some embodiments, the vanes 10 can be monolithically formed with the proximally-facing surface of the flange 47. In other embodiments, the vanes 10 can be mechanically connected to the proximally-facing surface of the flange 47.

As shown in FIG. 4D, the vanes 10 can extend circumferentially about the longitudinal axis L in a manner such that adjacent vanes 10 circumferentially overlap. For example, the radially outer end 10b of one vane can circumferentially overlap with, and be disposed radially outward from, the radially inner end 10a of an adjacent vane. The vanes 10 can be prevented from contacting the drive unit 9 by the thrust bearing aspect of the segmented cone bearing. As the impeller assembly 4 rotates, the vanes 10 can pump blood radially out of the channels 34 in the segmented cone bearing and thereby increase net flow through the flow tube of the impeller shaft 5 and segmented cone bearing. As shown, blood can exit the flow tube of the impeller shaft 5 at a location proximal the primary impeller 6 and be driven radially out of the channels 34 by the vanes 10. In the illustrated embodiment, five (5) vanes 10 are used, but it should be appreciated that fewer than five or more than five vanes 10 can be used.

As shown in FIGS. 4A, 4C, and 5A, the secondary impeller 7 can have a proximal end 52 at a proximal edge of the vanes 10. Further as shown in FIGS. 3A and 3C, the drive unit 9 can have a distal end 53 at a distal end of the distally-projecting segments 33. As explained above, the distally projecting convex segments 33 can be received within the concave opening 32 of the rotor assembly 46. When the convex segments 33 are mated within the concave opening 32, the distal end 53 of the drive unit 9 is distal the proximal end 52 of the second impeller 7 (e.g., distal the proximal-most end of the rotor assembly 46) as shown, for example, in FIG. 7.

VI. Integrated Rotor Core

As explained herein, in some embodiments the flow tube of the impeller shaft 5, the concave opening 32 of the segmented cone bearing, and the secondary impeller 7 can be integrated into one part as an integrated rotor core 8. Advantages of this approach include, without limitation, simpler assembly (as described below) and minimization or reduction of joints between parts (particularly on the inner surface of the flow tube of the shaft 5). Beneficially, the primary impeller 6 can be disposed on (e.g., mounted on and secured to (e.g., welded to or adhered to)) the impeller shaft 5, which can provide a compact design.

In various embodiments, therefore, the primary impeller 6 and the impeller shaft 5 may be separate components, with the impeller 6 mechanically connected to the impeller shaft 5. In other embodiments, the primary impeller 6 and impeller shaft 5 can comprise a unitary or monolithic structure (e.g., a molded or cast structure). Such unitary or monolithic structures can be formed without seams or joints between the components of the unitary or monolithic structure. Similarly, the secondary impeller 7 can be disposed on (e.g., mechanically secured to) the proximal end of the impeller shaft 5. In some embodiments, the secondary impeller 7 can be monolithically formed with the impeller shaft 5 so as to form a unitary component (e.g., molded, cast, etc.). In other embodiments, the secondary impeller 7 and the impeller shaft 5 can comprise separate components. In some embodiments, the primary impeller 6, the secondary impeller 7 (including the flange 47), and the impeller shaft 5 can form a unitary or monolithic component or body. In some embodiments, for example, the primary impeller 6, the secondary impeller 7, and the impeller shaft 5 can be injection molded over the rotor magnet 12. Where the secondary impeller 5 is molded over the magnet 12, the surface on which the secondary impeller 6 is disposed can be considered a flange where the surface extends radially outward from a lumen formed in a central portion of the molded part. Beneficially, as explained above, the integrated rotor core 8 can form a compact structure. Rotation of the drive magnet 17 can impart rotation to the rotor magnet 12, which is also disposed on (e.g., mechanically connected or mounted on) the impeller shaft 5. Rotation of the rotor magnet 12 can impart common rotation to the impeller shaft 5, the primary impeller 6, and the secondary impeller 7.

VII. Example Assembled Blood Flow Assist System

FIGS. 7 and 8A-8D show an example schematic view various features of the blood flow assist system 1 described herein. The features described above may also be combined in other ways.

Figure 7:
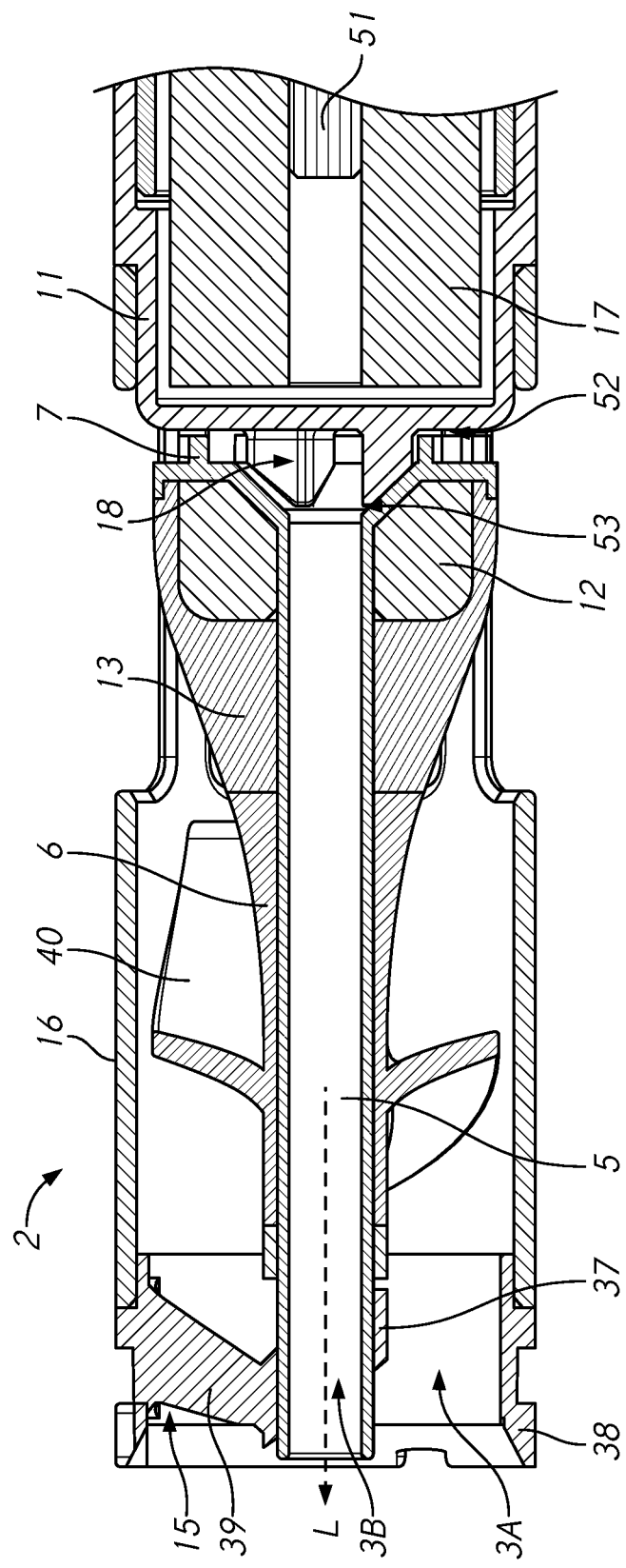
FIG. 7 is a schematic side sectional view of a pump according to various embodiments.
Figure 8D:
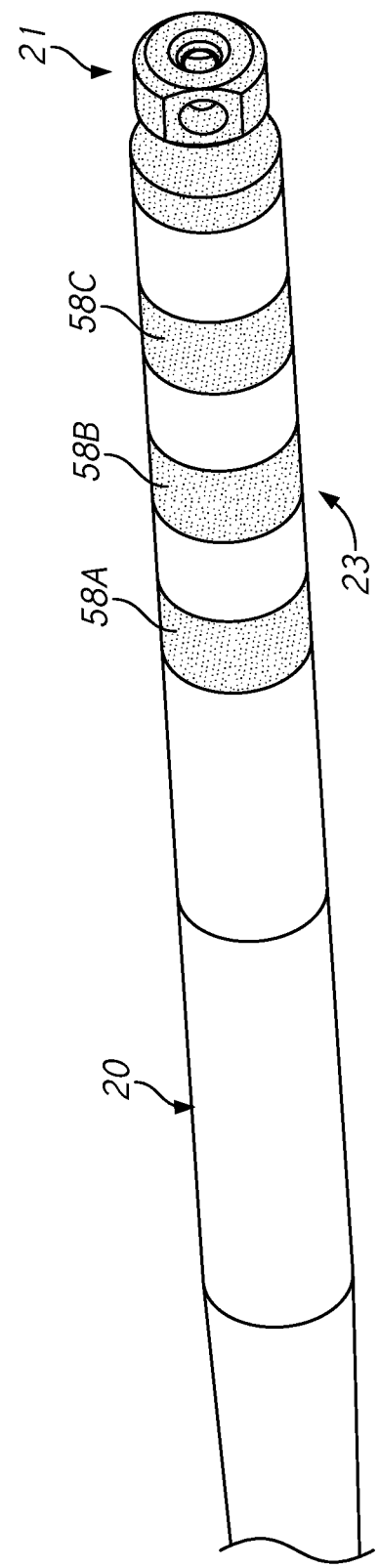
FIG. 8D is a schematic perspective view of a proximal end portion of the power wire.

As shown in FIGS. 7 and 8A, the system 1 comprises the drive unit 9 with the motor 30 that can be sealed in the motor housing 29. The drive magnet 17 can be rotatable by the motor 30 by way of a motor shaft 51. The motor 30 can electrically connect to the power wire 20. As shown in FIGS. 8A and 8C, the power wire 20 can comprise an insulating body having a central lumen 55 and a plurality of (e.g., three) outer lumens 56A-56C extending along a length of the power wire 20. The outer lumens 56A-56C can be sized and shaped to receive corresponding electrodes or electrical wire (not shown) to provide electrical power to the motor 30. For example, the lumens 56A-56C can receive, respectively, a hot electrode or wire, a neutral electrode or wire, and a ground electrode or wire. The electrodes can extend through corresponding openings 57A-57C of a motor mounting support 54 configured to support the motor 30. The central lumen 55 can be sized and shaped to receive an elongate stiffening member or guidewire (not shown). The stiffening member or guidewire can be inserted into the central lumen 55 to help guide the pump 2 to the treatment location. As shown in FIG. 8D, the connector 23 near the proximal end 21 of the system 1 can have electrical contacts 58A-58C electrically connected to the electrodes in the corresponding outer lumens 56A-56C. The contacts 58A-58C can comprise rings spaced apart by an insulating material and can be configured to electrically connect to corresponding electrical components in the control system or console (not shown).

The drive magnet 17 can be sealed within the drive unit 9 by the drive unit cover 11 that may also have features that act as the bearing components (e.g., the distally-projecting segments 33). In some embodiments, the top distal portion of the cover 11 may provide the segments 33 forming the conical member 45 of the segmented cone bearing as described in this disclosure. The corresponding conical opening 32 of this bearing pair can be built into a rotatable piece that comprises the secondary impeller 7 and flow tube or impeller shaft 5 (together, the integrated rotor core 8). The convex member 45 matches the contour and fits inside of the concave opening 32 of the rotatable piece. The channels 34 in the segmented cone bearing provide fluid passages for blood entering the bearing region through the flow tube 5 and forced out of the bearing region by the secondary impeller 7. A lubricating layer of blood between the bearing surfaces of the integrated rotor core 8 and the matching surfaces of the cone segments 33 provides lubrication, reduces wear, and eases relative motion of the two components. Depending on the geometry, rotational speed, and materials making up the interface, this may be hydrodynamic, elastohydrodynamic, boundary, or mixed lubrication.

The rotor magnet 12 of the rotor assembly 46 can be positioned on the integrated rotor core 8 to be in close proximity to the drive unit 9, thereby allowing the integrated rotor core 8 to be magnetically coupled to the drive unit 9 and rotated as desired. The first or primary impeller 6 with an integrated streamlined fairing 13 can be is placed over the rotor magnet 12 and joined to the integrated rotor core 8 to at least partially form the pump rotor assembly 46. The three-piece construction (integrated rotor core 8, magnet, and primary impeller 6 with integrated fairing) can have advantages as discussed previously related to ease of construction and compact design. In some embodiments, the portion of the primary impeller 6 that interfaces with the flow tube 5 may be shaped to function as a thrust pad or to be fit with a separate thrust ring 14 to interface with a matching thrust pad on the sleeve bearing 15 that fits around the flow tube 5. The rotor magnet 12 and primary impeller 6 with the fairing 13 may be secured to the integrated rotor core 8 so that the components rotate together.

Alternatively, the pump rotor could be assembled from more than three pieces. In one alternative embodiment, the primary impeller 6 and the fairing 13 are separate pieces. This can allow the primary impeller 6 and the fairing 13 to be made of different materials. Alternatively, the rotor magnet 12 may be coated to be suitable for blood contact and may not be covered by the fairing 13, but rather directly joined to the primary impeller 6. Such a configuration may allow use of a larger diameter magnet (with corresponding higher torque coupling) in the same pump rotor diameter than would be possible with a magnet inside a fairing.

In another alternative embodiment, a separate ring 14 may be added around the flow tube 5 above the primary impeller 6. This separate ring would then serve as the thrust interface that mates with the thrust surface of the sleeve bearing. The separate ring could be made of a different material than the flow tube 5 or primary impeller 6.

The flow tube of the impeller shaft 5 of the pump rotor can fit inside a fixed (non-rotating) sleeve bearing 15 (FIG. 7). As explained above, the sleeve bearing 15 can provide radial confinement of the impeller assembly 4 and the rotor assembly 46. The bearing interface comprises the outer surface of the impeller shaft 5 and the inner surface of the sleeve bearing 15. The sleeve bearing 15 can have a modified geometry as explained above that reduces or minimizes continuous coverage of the outer surface of the impeller shaft 5 and thereby reduces the potential for thrombosis. The sleeve bearing 15 may also optionally provide a thrust bearing surface that interfaces with the optional thrust bearing surface of the primary impeller 6 or optional thrust ring 14.

The outer bearing carrier 38 of the sleeve bearing 15 can attach to the shroud 16 that fits around the impeller assembly 4 and is attached to the drive unit cover 11 of the drive unit 9. The connecting structure 39 can include an arm or arms may attach directly to the shroud 16 or may attach to a ring that is then attached to the shroud 16 to provide improved rigidity and circularity of the shroud 16.

The shroud 16 can comprise a tube with an inlet end and an outlet end. The shroud 16 can be placed over the various internal components that make up the pump rotor (e.g., the impeller assembly 4 and the rotor assembly 46). The outlet end of the shroud 16 can be secured to the drive unit cover 11 of the drive unit 9. The inlet side of the shroud 16 can be open to create an inlet port 27. The front bearing is placed within the inlet port of the shroud 16 as described above. The outlet side of the shroud 16 has openings 25 in the surface of the shroud (outlet ports) that provide outlets for fluid driven by the primary impeller 6 and secondary impeller 7.

While some drawings of the system are shown without struts for clarity, the pump may include struts or any other securing means for securing the pump in the circulatory system, such as illustrated in U.S. Pat. Nos. 8,012,079 and 9,572,915 and U.S. Pat. Pub. No. 2017/0087288.

VIII. Operation

As shown in FIGS. 9A and 9B, various embodiments of the pump 2 provide two flow paths 3A, 3B as explained herein. The first flow pathway 3A (red in FIGS. 9A-9B) is driven by the primary impeller 6, which draws fluid in through the inlet port 27 of the shroud 16 and directs the fluid out of the outlet ports 25 of the shroud 16. The second flow path 3B (yellow in FIG. 9A and blue in FIG. 9B) is driven by the secondary impeller 7, which draws fluid through the internal secondary flow path 3B, e.g., a lumen or flow tube of the impeller shaft 5. The internal flow path passes through the flow tube of the shaft 5 of the integrated rotor core 8. As the fluid reaches the proximal end 5B of the shaft 5, some of the fluid passes through the channels 34 between the cone segments 33 and a smaller fraction passes between the matching conical surfaces of the bearing interfaces (e.g., between the convex member 45 and the concave opening or cavity 32). The fluid can be driven radially outward by the vanes 10 of the secondary impeller 7. Notably, flow from both flow paths can be directed from the inlet 27 to the outlet 25 in the illustrated embodiment. In other embodiments, as described herein, the flow of blood can be reversed.

It shall be apparent to one of ordinary skill in the art that fluid flowing through the secondary flow path, particularly the fluid layer between the matching cone bearing interface surfaces, acts as a lubricating layer between the rotor assembly 46 and the fixed segments 33 of the segmented cone bearing. Further, the matching conical surfaces of the segmented cone bearing can provide both axial and radial confinement of the pump assembly 46.

IX. Advantages

Various embodiments disclosed herein can have a number of unique advantages. Many of these advantages are described herein, but they are not an exhaustive list. The following are only additional non-limiting examples of advantages, one or more of which can apply to particular embodiments.
  a. Bearing elements (e.g., the sleeve bearing 15, 15A, 15B and/or the segmented cone bearing) can have surface area contact rather than point contact or line contact.
  b. Secondary flow along the second pathway 3B may be in the same direction as the primary flow pathway 3A to reduce or to minimize potential recirculation of blood.
  c. The flow tube or shaft 5, conical opening 32 of segmented cone bearing, and the secondary impeller 7 can be beneficially integrated in an integrated rotor core 8.
  d. Attractive force of the magnetic coupling utilizes a thrust bearing in only one direction to support the external rotor; no thrust bearing may be used to prevent movement of the pump rotor 8 away from the drive unit 9.

Embodiments described herein are included to demonstrate particular aspects of the present disclosure. It should be appreciated by those of ordinary skill in the art that the embodiments described herein merely represent non-limiting embodiments of the disclosure. Those of ordinary skill in the art should, in light of the present disclosure, appreciate that many changes can be made in the specific embodiments described, including various combinations of the different elements, components, steps, features, or the like of the embodiments described, and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted fairly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A blood flow assist system comprising:
    an impeller assembly comprising:
        a rotatable member;
        a first impeller being a separate piece from and interfacing with an outer surface of the rotatable member, the first impeller configured to pump blood along a first flow pathway along an exterior surface of the first impeller, a majority of the blood flowing along the first flow pathway being directed along a longitudinal axis of the blood flow assist system; and
        a second impeller disposed on the rotatable member spaced apart proximally from the first impeller along the rotatable member, the second impeller configured to direct blood radially outward relative to the longitudinal axis from a second flow pathway in a lumen of the rotatable member, the second impeller disposed on a generally proximally-facing surface of the rotatable member.

2. The blood flow assist system of claim 1, further comprising a drive unit configured to impart rotation to the rotatable member, the drive unit having a distal end disposed distal a proximal end of the second impeller, wherein the drive unit comprises a drive magnet, the blood flow assist system further comprising a drive bearing between the drive magnet and the impeller assembly, the drive bearing comprising a convex bearing surface having a plurality of distally-projecting segments, the plurality of distally-projecting segments spaced apart circumferentially to define at least one channel between adjacent segments, the second flow pathway comprising the at least one channel.

3. The blood flow assist system of claim 1, further comprising a sleeve bearing disposed about the rotatable member at a location distal the first impeller, wherein, in a cross-section taken perpendicular to an axis of rotation of the first impeller, a bearing surface of the sleeve bearing is disposed about only a portion of a perimeter of the rotatable member at a selected axial location, such that, when the rotatable member is rotated about the axis of rotation, an exterior surface of the rotatable member at the selected axial location is cyclically exposed to blood during operation of the blood flow assist system.

4. The blood flow assist system of claim 1, further comprising a pump housing, the impeller assembly disposed at least partially within the pump housing.

5. The blood flow assist system of claim 4, further comprising a support structure coupled with the pump housing, the support structure comprising struts configured to contact a blood vessel wall to maintain spacing of the pump housing from a blood vessel wall in which the pump housing is disposed.

6. The blood flow assist system of claim 1, wherein the rotatable member further comprises an impeller shaft and a flange extending radially outward from the impeller shaft, wherein the impeller shaft, the second impeller, and the flange form an integrated rotor core, the first impeller attached to the impeller shaft.

7. The blood flow assist system of claim 1, wherein the rotatable member, the first impeller, and the second impeller form a unitary body.

8. A kit comprising:
    the blood flow assist system of claim 1 and further comprising:
        a motor assembly configured to impart rotation to the first impeller and the second impeller; and
        a power wire electrically connected to the motor assembly; and
    a console configured to electrically connect to the power wire.

9. The blood flow assist system of claim 1, wherein the rotatable member is free of obstructions within the lumen constricting blood flow within the second flow pathway.

10. The blood flow assist system of claim 1, wherein the rotatable member further comprises an impeller shaft and a flange extending radially outward from the impeller shaft, an inner periphery of the first impeller disposed on an outer periphery of the impeller shaft, the flange extending radially beyond the outer periphery of the impeller shaft.

11. A blood flow assist system comprising:
    an impeller assembly comprising:
        an impeller shaft comprising a circular right cylinder forming a constant inner diameter lumen extending proximally from a distal end thereof;
        a first impeller extending outward from the impeller shaft; and
        a second impeller disposed on the impeller shaft spaced apart proximally from the first impeller along the impeller shaft; and
    a drive unit configured to impart rotation to the impeller shaft, the drive unit having a distal end disposed distal a proximal end of the second impeller within a concave opening at a proximal end portion of the impeller shaft, the concave opening defined within a conical surface extending from a proximal end of the constant inner diameter lumen.

12. The blood flow assist system of claim 11, wherein the first impeller is configured to pump blood along a first flow pathway along an exterior surface of the first impeller, a majority of the blood flowing along the first flow pathway being directed along a longitudinal axis of the blood flow assist system.

13. The blood flow assist system of claim 11, further comprising a fairing disposed about the impeller shaft between the first impeller and the second impeller, the first flow pathway disposed along an angled exterior surface of the fairing.

14. The blood flow assist system of claim 11, further comprising a second flow pathway through a lumen of the impeller shaft, the second impeller configured to direct blood from the second flow pathway radially outward relative to the longitudinal axis.

15. The blood flow assist system of claim 14, wherein, during operation of the blood flow assist system, blood pumped along the second flow pathway flows between a proximal end portion of the impeller shaft and the distal end of the drive unit.

16. The blood flow assist system of claim 15, wherein the drive unit comprises a drive magnet and a drive bearing between the drive magnet and the impeller assembly, the drive bearing comprising a convex bearing surface having a plurality of distally-projecting segments, the plurality of distally-projecting segments spaced apart circumferentially to define at least one channel between adjacent segments, the secondary flow pathway comprising the at least one channel.

17. The blood flow assist system of claim 11, further comprising a flange extending non-parallel from a proximal end portion of the impeller shaft, the second impeller disposed comprising a plurality of vanes on a generally proximally-facing surface of the flange.

18. The blood flow assist system of claim 17, wherein the conical opening extends inwardly and distally relative to the generally proximally-facing surface of the flange, wherein the drive unit comprises a convex member sized to fit within the conical opening.

19. The blood flow assist system of claim 17, further comprising a rotor magnet coupled to the impeller shaft, the rotor magnet disposed adjacent a distally-facing surface of the flange.

20. The blood flow assist system of claim 11, further comprising a sleeve bearing disposed about the impeller shaft at a location distal the first impeller, wherein, in a cross-section taken perpendicular to an axis of rotation of the first impeller, a support surface of the sleeve bearing is disposed about only a portion of a perimeter of the impeller shaft at a selected axial location, such that, when the impeller shaft is rotated about the axis of rotation, an exterior surface of the impeller shaft at the selected axial location is cyclically exposed to blood during operation of the blood flow assist system.

21. The blood flow assist system of claim 11, further comprising a pump housing, the impeller assembly disposed at least partially within the pump housing, wherein the pump housing includes an outlet, the outlet disposed proximal the first impeller.

22. The blood flow assist system of claim 21, wherein the second impeller is disposed proximal a distal end of the outlet.

23. The blood flow assist system of claim 11, further comprising a pump housing and a support structure coupled to or formed with the pump housing, the impeller assembly disposed at least partially within the pump housing, the support structure comprising struts configured to contact a blood vessel wall to maintain spacing of the pump housing from a blood vessel wall in which the pump housing is disposed.

24. The blood flow assist system of claim 11, wherein the first impeller comprises a plurality of outwardly-extending, axially-aligned blades.

25. A blood flow assist system comprising:
a rotatable member having an outer surface and an inner surface extending along a longitudinal axis of the blood flow assist system;
a first impeller having an inside surface disposed on the outer surface of the rotatable member; and
a second impeller disposed on the rotatable member spaced apart proximally from the first impeller along the rotatable member;
wherein the second impeller is disposed on a proximally-facing surface of the rotatable member, the proximally facing surface extending radially beyond the outer surface of the rotatable member upon which the first impeller is disposed.

26. The blood flow assist system of claim 25, wherein the first impeller is configured to pump blood along a first flow pathway along an exterior surface of the first impeller, a majority of the blood flowing along the first flow pathway being directed along a longitudinal axis of the blood flow assist system, the blood flow assist system further comprising a second flow pathway through a lumen of the rotatable member, the second impeller configured to direct blood from the second flow pathway radially outward relative to the longitudinal axis.

27. The blood flow assist system of claim 25, further comprising a drive unit configured to impart rotation to the rotatable member, the drive unit having a distal end disposed distal a proximal end of the second impeller, wherein the drive unit comprises a drive magnet and a drive bearing between the drive magnet and the second impeller, the drive bearing comprising a convex bearing surface having a plurality of distally-projecting segments, the plurality of distally-projecting segments spaced apart circumferentially to define at least one channel between adjacent segments.

28. The blood flow assist system of claim 25, further comprising a drive unit bearing comprising a segmented convex bearing surface, wherein the rotatable member comprises a conical opening disposed between the inner surface and the proximally-facing surface of the rotatable member, the conical opening configured to receive the segmented convex bearing surface.

29. The blood flow assist system of claim 28, wherein the distal end of the drive unit is disposed proximal a proximal end of the first impeller.

30. The blood flow assist system of claim 28, wherein the segmented convex bearing comprises a central hollow configured to receive blood flowing along the inner surface of the rotatable member within an internal flow path, the secondary impeller driving blood from the central hollow radially outward between adjacent segments of the segmented convex bearing.

* * * * *